(12) United States Patent
Inagaki et al.

(10) Patent No.: US 9,161,538 B2
(45) Date of Patent: Oct. 20, 2015

(54) PYRIDINE COMPOUND AND AGRICULTURAL FUNGICIDE

(71) Applicant: Nippon Soda Co., Ltd., Chiyoda-ku, Tokyo (JP)

(72) Inventors: Jun Inagaki, Kanagawa (JP); Homare Yamanaka, Kanagawa (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 14/414,546

(22) PCT Filed: Jul. 12, 2013

(86) PCT No.: PCT/JP2013/069181
§ 371 (c)(1),
(2) Date: Jan. 13, 2015

(87) PCT Pub. No.: WO2014/013951
PCT Pub. Date: Jan. 23, 2014

(65) Prior Publication Data
US 2015/0189878 A1 Jul. 9, 2015

(30) Foreign Application Priority Data
Jul. 19, 2012 (JP) ................................. 2012-160583

(51) Int. Cl.
| C07D 213/82 | (2006.01) |
| C07D 405/12 | (2006.01) |
| A01N 43/40 | (2006.01) |
| A01N 47/18 | (2006.01) |
| A01N 43/56 | (2006.01) |
| A01N 43/713 | (2006.01) |
| A01N 43/78 | (2006.01) |
| C07D 401/12 | (2006.01) |
| C07D 409/12 | (2006.01) |
| C07D 417/12 | (2006.01) |

(52) U.S. Cl.
CPC ............... *A01N 43/40* (2013.01); *A01N 43/56* (2013.01); *A01N 43/713* (2013.01); *A01N 43/78* (2013.01); *A01N 47/18* (2013.01); *C07D 213/82* (2013.01); *C07D 401/12* (2013.01); *C07D 405/12* (2013.01); *C07D 409/12* (2013.01); *C07D 417/12* (2013.01)

(58) Field of Classification Search
None
See application file for complete search history.

(56) References Cited

U.S. PATENT DOCUMENTS

| 2007/0105943 A1 | 5/2007 | Nakamoto et al. |
| 2009/0227799 A1 | 9/2009 | Nakamoto et al. |
| 2011/0009454 A1 | 1/2011 | Matsuzaki et al. |

FOREIGN PATENT DOCUMENTS

| JP | 05-230016 A | 9/1993 |
| JP | 2008-500336 A | 1/2008 |
| JP | 2010-526035 A | 7/2010 |
| WO | WO 2005/033079 A1 | 4/2005 |
| WO | WO 2005/115986 A1 | 12/2005 |
| WO | WO 2006/016548 A1 | 2/2006 |
| WO | WO 2008/128711 A1 | 10/2008 |
| WO | WO 2009/107764 A1 | 9/2009 |
| WO | WO 2012/052167 A1 | 4/2012 |

OTHER PUBLICATIONS

Bernat et al, Chemical Abstracts 157:454456 , (2012), Abstract of ChemMedChem (2012), 7(8), 1481-1489.*
Bernat et al, ChemMedChem (2012), 7(8), pp. 1481-1489.*
International Search Report dated Aug. 27, 2013, in PCT/JP2013/069181.
Madkour et al., "Reactions of 5-(p-anisyl)-2-methyl-7-(p-tolyl)-4H-pyrido-[2,3-d][1,3]oxazin-4-one," Heterocycles, 1994, 38(1):57-69.

* cited by examiner

*Primary Examiner* — Zinna Northington Davis
(74) *Attorney, Agent, or Firm* — Foley & Lardner LLP

(57) ABSTRACT

The present invention provides an agricultural fungicide having definitive effects which can be safely used, and a pyridine compound or salts thereof useful as an active ingredient of an agricultural fungicide. The pyridine compound or salts thereof of the present invention are represented by the following formula. In the formula, $R^1$ represents a formyl group or the like, $R^2$ represents a hydrogen bond or the like, each of $R^3$, $R^4$, and $R^5$ independently represents a hydrogen atom, E represents a phenyl group or the like, A represents a halogen atom, and n is any integer of 0 to 5.

[Chem. 1]

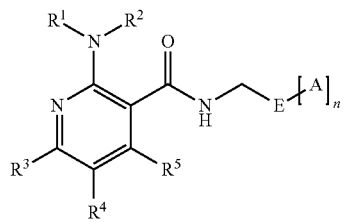

5 Claims, No Drawings

PYRIDINE COMPOUND AND AGRICULTURAL FUNGICIDE

TECHNICAL FIELD

The present invention relates to an agricultural fungicide having definitive effects which can be safely used and a pyridine compound useful as an active ingredient of an agricultural fungicide.

CROSS-REFERENCE TO RELATED APPLICATIONS

This application is a National Stage application of PCT/JP2013/069181, filed Jul. 12, 2013, which claims priority from Japanese Patent Application No. 2012-160583, filed Jul. 19, 2012, the content of which is incorporated herein by reference.

BACKGROUND ART

A large number of control drugs are used against diseases of agricultural crops. However, in many control drugs in the related art, the control efficacy thereof is insufficient, use thereof is limited by the appearance of a drug-resistant pathogen, phytotoxicity to plants or contamination is caused, or toxicity to human bodies, animals, and fish or influence on the environment is great, and thus, control drugs in the related art cannot be fully satisfied. Therefore, drugs having no such drawback have been strongly demanded.

In connection with the present invention, PTL 1 discloses an agricultural fungicide containing the compound represented by the formula (A) and the like as an active ingredient.

[Chem. 1]

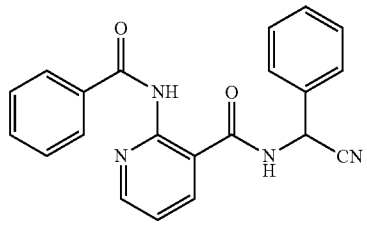

(A)

PTLs 2 and 3 disclose the compound represented by the formula (B) and the like as a Glycosylphosphatidylinositol (GPI) biosynthesis inhibitor, and it is described that these are effective as an antimalarial drug and an antimycotic drug, respectively.

[Chem. 2]

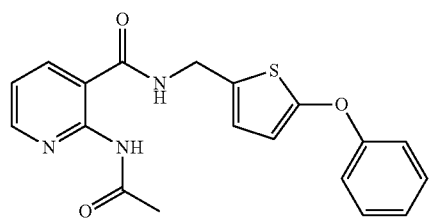

(B)

PTL 4 discloses compounds having an analgesic effect such as the compound represented by the formula (C).

[Chem. 3]

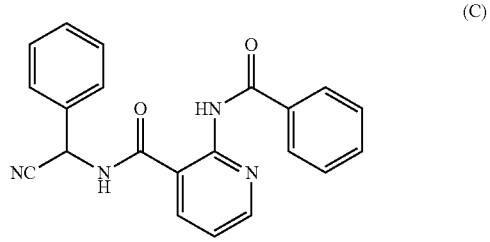

(C)

In addition, PTL 5 discloses the compound represented by the formula (D) as a synthetic intermediate of an analgesic drug.

[Chem. 4]

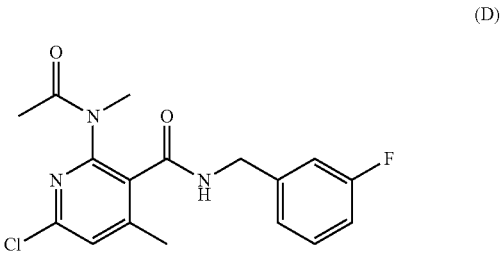

(D)

PTL 6 discloses insecticides including the compound represented by the formula (E) and the like.

[Chem. 5]

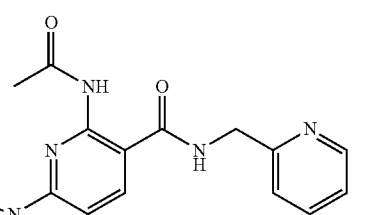

(E)

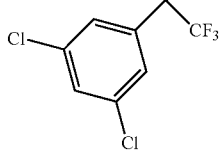

NPL 1 describes the compound represented by the formula (F) as a synthetic intermediate of a medicine compound.

[Chem. 6]

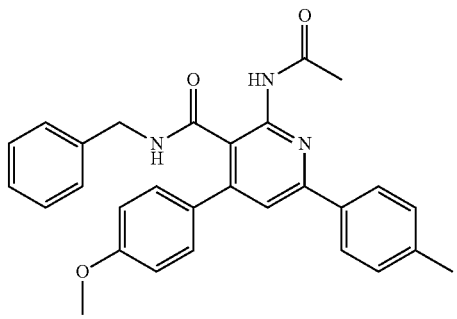

(F)

CITATION LIST

Patent Literature

[PTL 1] Japanese Unexamined Patent Application First Publication No. H5-230016
[PTL 2] PCT International Publication No. WO2006/016548
[PTL 3] PCT International Publication No. WO2005/033079
[PTL 4] Published Japanese Translation No. 2008-500336 of the PCT International Publication
[PTL 5] PCT International Publication No. WO2012/052167
[PTL 6] Published Japanese Translation No. 2010-526035 of the PCT International Publication Non-Patent Literature

[NPL 1] Madkour et al. Heterocycles 38 (1994) 57-69

SUMMARY OF THE INVENTION

Problems to be Solved by the Invention

An object of the invention is to provide an agricultural fungicide having definitive effects which can be safely used, and a pyridine compound or salts thereof useful as an active ingredient of an agricultural fungicide.

Means for Solving the Problems

The inventors have carried out thorough studies in order to achieve the above object. As a result, the pyridine compound represented by the formula (1) and salts thereof were obtained. Furthermore, it was found that the pyridine compound has definitive effects, and can be safely used as an active ingredient of an agricultural fungicide. The present invention has been completed by further consideration on the basis of these findings.

That is, the present invention includes the following aspects. [1] A pyridine compound represented by the formula (1) or salts thereof.

[Chem. 7]

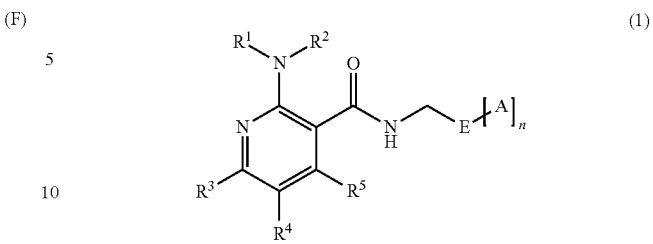

(1)

[In the formula (1),
$R^1$ represents a formyl group, a C1-8 alkylcarbonyl group which is unsubstituted or has a substituent, a C3-8 cycloalkylcarbonyl group which is unsubstituted or has a substituent, a C6-10 arylcarbonyl group which is unsubstituted or has a substituent, a 5 to 10-membered heterocyclic carbonyl group which is unsubstituted or has a substituent, a C3-8 cycloalkyl C1-6 alkylcarbonyl group which is unsubstituted or has a substituent, a C6-10 aryl C1-6 alkylcarbonyl group which is unsubstituted or has a substituent, a 5 to 10-membered heterocyclic C1-6 alkylcarbonyl group which is unsubstituted or has a substituent, a C1-8 alkyloxycarbonyl group which is unsubstituted or has a substituent, a C3-8 cycloalkyloxycarbonyl group which is unsubstituted or has a substituent, a C6-10 aryloxycarbonyl group which is unsubstituted or has a substituent, a 5 to 10-membered heterocyclic oxycarbonyl group which is unsubstituted or has a substituent, a C1-8 alkylthiocarbonyl group which is unsubstituted or has a substituent, a di C1-8 alkylsulfamoyl group which is unsubstituted or has a substituent, a C1-8 alkylsulfonyl group which is unsubstituted or has a substituent, a C3-8 cycloalkylsulfonyl group which is unsubstituted or has a substituent, a C6-10 arylsulfonyl groups which is unsubstituted or has a substituent, or a 5 to 10-membered heterocyclic sulfonyl group which is unsubstituted or has a substituent.
$R^2$ represents a hydrogen atom, a C1-8 alkyl group which is unsubstituted or has a substituent, or a C1-8 alkylcarbonyl group which is unsubstituted or has a substituent.
Each of $R^3$, $R^4$, and $R^5$ independently represents a hydrogen atom, a C1-8 alkyl group which is unsubstituted or has a substituent, or a halogen atom.
E represents a furyl group, a pyrrolyl group, a tetrazolyl group, a thiazolyl group, a pyrazolyl group, a phenyl group, or a pyridyl group.
A represents a halogen atom, a cyano group, a C1-8 alkyl group which is unsubstituted or has a substituent, a C1-8 alkoxy group which is unsubstituted or has a substituent, a C3-8 cycloalkyl group which is unsubstituted or has a substituent, a C3-8 cycloalkoxy group which is unsubstituted or has a substituent, a C6-10 aryl group which is unsubstituted or has a substituent, a C6-10 aryloxy group which is unsubstituted or has a substituent, a 5 to 10-membered heterocyclic group which is unsubstituted or has a substituent, or a 5 to 10 membered heterocyclyloxy group which is unsubstituted or has a substituent.
n represents the number of A, and is any integer of 0 to 5. When n is equal to or greater than 2, A's may be the same as or different from each other.]
[2] The pyridine compound or salts thereof according to [1], in which in the formula (1), E is a phenyl group.
[3] The pyridine compound or salts thereof according to [1] or [2], in which in the formula (1), A is any one of a cyano group, a C1-8 alkyl group which is unsubstituted or has a substituent, a C1-8 alkoxy group which is unsubstituted or has a substituent, a phenyl group which is unsubstituted or has a substituent, a phenoxy group which is unsubstituted or has a substituent, a 5 or 6-membered heteroaryl group which is unsubstituted or has a substituent, or a 5 or 6-membered heteroaryloxy group which is unsubstituted or has a substituent, and n is any integer of 1 to 5.

[4] The pyridine compound or salts thereof according to any one of [1] to [3], in which in the formula (1), $R^3$ is a hydrogen atom or a C1-8 alkyl group which is unsubstituted or has a substituent.

[5] An agricultural fungicide containing at least one selected from the pyridine compound or salts thereof according to any one of [1] to [4] as an active ingredient.

Advantageous Effects of the Invention

A pyridine compound or salts thereof of the present invention are useful novel compounds as an active ingredient of an agricultural fungicide.

The agricultural fungicide of the present invention has definitive and excellent control effects, does not cause phytotoxicity to plants, exhibits low toxicity to human bodies, animals, and fish, has little influence on the environment, and is a safe drug.

Embodiments of the Invention

Hereinafter, the present invention will be described in detail by dividing into two sections of 1) a pyridine compound and 2) an agricultural fungicide.

1) Pyridine Compound

[Pyridine Compound Represented by Formula (1)]

The pyridine compound according to the present invention is a compound (hereinafter, referred to as "compound (1) in some cases) represented by the formula (1).

[Chem. 8]

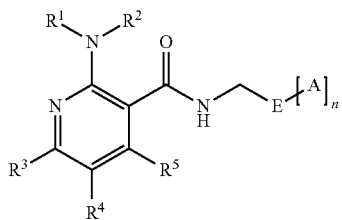

(1)

[In the formula (1), $R^1$ represents a formyl group, a C1-8 alkylcarbonyl group which is unsubstituted or has a substituent, a C3-8 cycloalkylcarbonyl group which is unsubstituted or has a substituent, a C6-10 arylcarbonyl group which is unsubstituted or has a substituent, a 5 to 10-membered heterocyclic carbonyl group which is unsubstituted or has a substituent, a C3-8 cycloalkyl C1-6 alkylcarbonyl group which is unsubstituted or has a substituent, a C6-10 aryl C1-6 alkylcarbonyl group which is unsubstituted or has a substituent, a 5 to 10-membered heterocyclic C1-6 alkylcarbonyl group which is unsubstituted or has a substituent, a C1-8 alkyloxycarbonyl group which is unsubstituted or has a substituent, a C3-8 cycloalkyloxycarbonyl group which is unsubstituted or has a substituent, a C6-10 aryloxycarbonyl group which is unsubstituted or has a substituent, a 5 to 10-membered heterocyclic oxycarbonyl group which is unsubstituted or has a substituent, a C1-8 alkylthiocarbonyl group which is unsubstituted or has a substituent, a di C1-8 alkylsulfamoyl group which is unsubstituted or has a substituent, a C1-8 alkylsulfonyl group which is unsubstituted or has a substituent, a C3-8 cycloalkylsulfonyl group which is unsubstituted or has a substituent, a C6-10 arylsulfonyl groups which is unsubstituted or has a substituent, or a 5 to 10-membered heterocyclic sulfonyl group which is unsubstituted or has a substituent.

$R^2$ represents a hydrogen atom, a C1-8 alkyl group which is unsubstituted or has a substituent, or a C1-8 alkylcarbonyl group which is unsubstituted or has a substituent.

Each of $R^3$, $R^4$, and $R^5$ independently represents a hydrogen atom, a C1-8 alkyl group which is unsubstituted or has a substituent, or a halogen atom.

E represents a furyl group, a pyrrolyl group, a tetrazolyl group, a thiazolyl group, a pyrazolyl group, a phenyl group, or a pyridyl group.

A represents a halogen atom, a cyano group, a C1-8 alkyl group which is unsubstituted or has a substituent, a C1-8 alkoxy group which is unsubstituted or has a substituent, a C3-8 cycloalkyl group which is unsubstituted or has a substituent, a C3-8 cycloalkoxy group which is unsubstituted or has a substituent, a C6-10 aryl group which is unsubstituted or has a substituent, a C6-10 aryloxy group which is unsubstituted or has a substituent, a 5 to 10-membered heterocyclic group which is unsubstituted or has a substituent, or a 5 to 10 membered heterocyclyloxy group which is unsubstituted or has a substituent.

n represents the number of A, and is any integer of 0 to 5. When n is equal to or greater than 2, A's may be the same as or different from each other.]

First meaning of "unsubstituted" and "have a substituent" in the formula (1) will be described.

The term "unsubstituted" means that only a group which is a base skeleton is present. When only the name of a group which is a base skeleton is described without describing "have a substituent", it means "unsubstituted" unless specified otherwise.

On the other hand, the term "have a substituent" means that any hydrogen atom of a group which is a base skeleton is substituted with a group having the same structure as or different from the base skeleton. Therefore, "a substituent" is another group which is bonded to a group which is a base skeleton. The substituent may be one, or two or more. Two or more substituents may be the same as or different from each other.

The term "C1-6" represents that the carbon atom number of a group which is a base skeleton is 1 to 6. The carbon atom number does not include the number of carbon atom present in a substituent. For example, a butyl group having an ethoxy group as a substituent is classified as a C2 alkoxy C4 alkyl group.

"Substituent" is not particularly limited as long as it is chemically acceptable and has the effect of the present invention.

Examples of a group which can be a "substituent" include halogen groups such as a fluoro group, a chloro group, a bromo group, and an iodo group; C1-6 alkyl groups such as a methyl group, an ethyl group, an n-propyl group, an i-propyl group, an n-butyl group, an s-butyl group, an i-butyl group, a t-butyl group, an n-pentyl group, and an n-hexyl group; C3-6 cycloalkyl groups such as a cyclopropyl group, a cyclobutyl group, a cyclopentyl group, and a cyclohexyl group; C2-6 alkenyl groups such as a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group; C3-6 cycloalkenyl groups such as a 2-cyclopropenyl group, a 2-cyclopentenyl group, and a 3-cyclohexenyl group; and C2-6 alkynyl groups such as an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, and a 1,1-dimethyl-2-butynyl group;

C1-6 alkoxy groups such as a methoxy group, an ethoxy group, an n-propoxy group, an i-propoxy group, an n-butoxy group, an s-butoxy group, an i-butoxy group, and a t-butoxy group; C2-6 alkenyl groups such as a vinyloxy group, an allyloxy group, a propenyloxy group, and a butenyloxy, C2-6 alkynyloxy groups such as an ethynylocy group and a propargyloxy group; C6-10 aryl group such as a phenyl group and a naphthyl group; C6-10 aryloxy groups such as a phenoxy group and 1-naphthoxy group; C7-11 aralkyl groups such as a benzyl group and a phenethyl group; C7-11 aralkyloxy groups such as a benzyloxy group and a phenethyloxy group; C1-7 acyl groups such as a formyl group, an acetyl group, a propionyl group, a benzoyl group, and a cyclohexylcarbonyl group; C1-7 acyloxy groups such as a formyloxy group, an acetyloxy group, a propionyloxy group, a benzoyloxy group, and a cyclohexylcarbonyl group; C1-6 alkoxycarbonyl groups such as a methoxycarbonyl group, an ethoxycarbonyl group, an n-propoxycarbonyl group, an i-propoxycarbonyl group, an n-butoxycarbonyl group, and t-butoxycarbonyl group; carboxyl group;

A hydroxyl group; an oxo group; C1-6 haloalkyl groups such as a chloromethyl group, a chloroethyl group, a trifluoromethyl group, a 1,2-dichloro-n-propyl group, a 1-fluoro-n-butyl group, and a perfluoro-n-pentyl group; C2-6 haloalkenyl groups such as a 2-chloro-1-propenyl group and a 2-fluoro-1-butenyl group; C2-6 haloalkynyl groups such as a 4,4-dichloro-1-butynyl group, a 4-fluoro-1-pentynyl group, and a 5-bromo-2-pentynyl group; C1-6 haloalkoxy groups such as a 2-chloro-n-propoxy group and a 2,3-dichloro-butoxy group; C2-6 haloalkenyloxy groups such as a 2-chloropropenyloxy group and a 3-bromobutenyloxy group; C6-10 haloaryl groups such as a 4-chlorophenyl group, a 4-fluorophenyl group, and a 2,4-dichlorophenyl group; C6-10 haloaryloxy groups such as a 4-fluorophenyloxy group and a 4-chloro-1-naphthoxy group; C1-7 haloacyl groups such as a chloroacetyl group, a trifluoroacetyl group, a trichloroacetyl group, and a 4-chlorobenzoyl group;

A cyano group; an isocyano group; a nitro group; an isocyanato group; a cyanato group; an azido group; an amino group; C1-6 alkyl amino groups such as a methyl amino group, a dimethyl amino group, and a diethyl amino group; C6-10 aryl amino groups such as an amino group and a naphthyl amino groups; C7-11 aralkyl amino groups such as a benzyl amino group and phenylethyl amino group; C1-7 acyl amino groups such as a formyl amino group, an acetyl amino group, a propanoyl amino group, a butyryl amino group, an i-propylcarbonyl amino group, and a benzoyl amino group; C1-6 alkoxycarbonyl amino groups such as a methoxycarbonyl amino group, an ethoxycarbonyl group, an n-propoxycarbonyl amino group, and an i-propoxycarbonyl amino group; a carbamoyl group; substituted carbamoyl groups such as a dimethylcarbamoyl group, a phenylcarbamoyl group, and an N-phenyl-N-methylcarbamoyl group; imino C1-6 alkyl groups such as an iminomethyl group, a (1-imino)ethyl group, and (1-imino)-n-propyl group; hydroxyimino C1-6 alkyl groups such as a hydroxyimino methyl group, a (1-hydroxyimino)ethyl group, and a (1-hydroxyimino)propyl group; C1-6 alkoxyimino C1-6 alkyl groups such as a methoxyimino methyl group and a (1-methoxyimino)ethyl group;

A mercapto group; an isothiocyanato group; a thiocyanato group; C1-6 alkylthio groups such as a methylthio group, an ethylthio group, an n-propylthio group, an i-propylthio group, an n-butylthio group, an i-butylthio group, an s-butylthio group, and a t-butylthio group; C2-6 alkenylthio groups such as a vinylthio based and an allylthio group; C2-6 alkynylthio groups such as an ethynylthio group and a propargylthio group; C6-10 arylthio groups such as a phenylthio group and a naphthylthio group; heteroarylthio groups such as a thiazolylthio group and a pyridylthio group; C7-11 aralkylthio groups such as a benzylthio group and a phenethylthio group; (C1-6 alkylthio) carbonyl groups such as a (methylthio)carbonyl group, an (ethylthio)carbonyl group, an (n-propylthio)carbonyl group, an (i-propylthio)carbonyl group, an (n-butylthio)carbonyl group, an (i-butylthio)carbonyl group, an (s-butylthio)carbonyl group, and a (t-butylthio) carbonyl group;

C1-6 alkylsulfinyl groups such as a methylsulfinyl group, an ethylsulfinyl group, and a t-butylsulfinyl group; C2-6 alkenylsulfinyl groups such as an allylsulfinyl group; C2-6 alkynylsulfinyl groups such as a propargylsulfinyl group; C6-10 arylsulfinyl groups such as a phenylsulfinyl group; heteroarylarylsulfinyl group such as a thiazolylsulfinyl group and a pyridylsulfinyl group; C7-11 aralkylsulfonyl groups such as a benzylsulfinyl group and a phenethylsulfonyl group; C1-6 alkylsulfonyl groups such as a methylsulfonyl group, an ethylsulfonyl group, and a t-butylsulfonyl group; C2-6 alkenylsulfonyl groups such as an allylsulfonyl group; C2-6 alkynylsulfonyl groups such as a propargylsulfonyl group; C6-10 arylsulfonyl groups such as a phenylsulfonyl group; heteroarylsulfonyl groups such as a thiazolylsulfonyl group and a pyridylsulfonyl group; C7-11 aralkylsulfonyl groups such as a benzylsulfonyl group and a phenethylsulfonyl group;

5-membered heteroaryl groups such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group; 6-membered heteroaryl groups such as a pyridyl group, a pyrazinyl group, a pyrimidinyl group, a pyridazinyl group, and a triazinyl group; saturated heterocyclic groups such as an aziridinyl group, an epoxy group, a pyrrolidinyl group, a tetrahydrofuranyl group, a piperidyl group, a piperazinyl group, and morpholinyl group; C1-6 alkylsilyl groups such as group a trimethylsilyl group, a triethylsilyl group, and a t-butyldimethylsilyl group; and a triphenylsilyl group.

In addition, these "substituents" may further have another "substituent" therein. For example, the substituent may be a group having an ethoxy group as another substituent in a butyl group as a substituent, that is, an ethoxy buthyl group.

[$R^1$]

$R^1$ represents a formyl group, a C1-8 alkylcarbonyl group which is unsubstituted or has a substituent, a C3-8 cycloalkylcarbonyl group which is unsubstituted or has a substituent, a C6-10 arylcarbonyl group which is unsubstituted or has a substituent, a 5 to 10-membered heterocyclic carbonyl group which is unsubstituted or has a substituent, a C3-8 cycloalkyl C1-6 alkylcarbonyl group which is unsubstituted or has a substituent, a C6-10 aryl C1-6 alkylcarbonyl group which is unsubstituted or has a substituent, a 5 to 10-membered heterocyclic C1-6 alkylcarbonyl group which is unsubstituted or has a substituent, a C1-8 alkyloxycarbonyl group which is unsubstituted or has a substituent, a C3-8 cycloalkyloxycarbonyl group which is unsubstituted or has a substituent, a C6-10 aryloxycarbonyl group which is unsubstituted or has a substituent, a 5 to 10-membered heterocyclic oxycarbonyl group which is unsubstituted or has a substituent, a C1-8 alkylthiocarbonyl group which is unsubstituted or has a substituent, a di C1-8 alkylsulfamoyl group which is unsubstituted or has a substituent, a C1-8 alkylsulfonyl group which is unsubstituted or has a substituent, a C3-8 cycloalkylsulfonyl group which is unsubstituted or has a substituent, a C6-10 arylsulfonyl groups which is unsubstituted or has a substituent, or a 5 to 10-membered heterocyclic sulfonyl group which is unsubstituted or has a substituent.

The "C1-8 alkylcarbonyl group" is a group obtained by bonding between a C1-8 alkyl group and a carbonyl group.

The "C1-8 alkyl group" which is bonded to a carbonyl group is a saturated hydrocarbon group configured of 1 to 8 carbon atoms. The C1-8 alkyl group may be linear or branched. Examples of the "C1-8 alkyl group" include a methyl group, an ethyl group, an n-propyl group, an n-butyl group, an n-pentyl group, an n-hexyl group, an n-heptyl group, an n-octyl group, an i-propyl group, an i-butyl group, an s-butyl group, a t-butyl group, an i-pentyl group, a neopentyl group, a 2-methylbutyl group, a 2,2-dimethylpropyl group, and an i-hexyl group. Among these, the C1-6 alkyl group is preferable.

Examples of the "C1-8 alkylcarbonyl group" include an acetyl group, a propionyl group, an n-propyl carbonyl group, an n-butyl carbonyl group, a pentanoyl group, a valeryl group, an octanoyl group, an i-propyl carbonyl group, an i-butyl carbonyl group, a pivaloyl group, and an isovaleryl group.

Examples of the "C1-8 alkyl group which has a substituent" bonded to a carbonyl group include cycloalkylalkyl groups such as a cyclopropylmethyl group, a 2-cyclopropylethyl group, a cyclopentylmethyl group, and a 2-cyclohexylethyl group, and preferably a C3-6 cycloalkyl C1-6 alkyl group;

Cycloalkenylalkyl groups such as a cyclopentenylmethyl group, a 3-cyclopentenylmethyl group, a 3-cyclohexenylmethyl group, and a 2-(3-cyclohexenyl)ethyl group, and preferably a C4-6 cycloalkenyl C1-6 alkyl group;

Haloalkyl groups such as a fluoromethyl group, a chloromethyl group, a bromomethyl group, a difluoromethyl group, a dichloromethyl group, a dibromomethyl group, a trifluoromethyl group, a trichloromethyl group, a tribromomethyl group, a 2,2,2-trifluoroethyl group, a 2,2,2-trichloroethyl group, a pentafluoroethyl group, a 4-fluorobutyl group, a 4-chlorobutyl group, a 3,3,3-trifluoropropyl group, a 2,2,2-trifluoro-1-trifluoromethylethyl group, a perfluorohexyl group, a perchlorohexyl group, a perfluorooctyl group, a perchlorooctyl group, a 2,4,6-trichlorohexyl group, a perfluorodecyl group, and a 2,2,4,4,6,6-hexachlorooctyl group, and preferably a C1-6 haloalkyl group;

Arylalkyl groups (aralkyl groups) such as a benzyl group, a phenethyl group, a 3-phenylpropyl group, a 1-naphthylmethyl group, and a 2-naphthylmethyl group, and preferably a C6-10 aryl C1-6 alkyl group;

Heteroarylalkyl groups such as a 2-pyridylmethyl group, a 3-pyridylmethyl group, a 4-pyridylmethyl group, a 2-(2-pyridyl)ethyl group, a 2-(3-pyridyl)ethyl group, a 2-(4-pyridyl) ethyl group, a 3-(2-pyridyl)propyl group, a 3-(3-pyridyl)propyl group, a 3-(4-pyridyl)propyl group, a 2-pyrazinylmethyl group, a 3-pyrazinylmethyl group, a 2-(2-pyrazinyl)ethyl group, a 2-(3-pyrazinyl)ethyl group, a 3-(2-pyrazinyl)propyl group, a 3-(3-pyrazinyl)propyl group, a 2-pyrimidylmethyl group, a 4-pyrimidylmethyl group, a 2-(2-pyrimidyl)ethyl group, a 2-(4-pyrimidyl)ethyl group, a 3-(2-pyrimidyl)propyl group, a 3-(4-pyrimidyl)propyl group, a 2-furylmethyl group, a 3-furylmethyl group, a 2-(2-furyl)ethyl group, a 2-(3-furyl) ethyl group, a 3-(2-furyl)propyl group, and a 3-(3-furyl)propyl group, and preferably a 5-6 membered heteroaryl C1-6 alkyl group;

Hydroxyalkyl groups such as a hydroxymethyl group, a 1-hydroxyethyl group, a 2-hydroxyethyl group, a 1-hydroxypropyl group, a 3-hydroxypropyl group, a 1-hydroxy-1-methylethyl group, a 2-hydroxy-1,1-dimethylethyl group, a 2-hydroxy-1,1-dimethylpropyl group, and a 2-hydroxy-2-methylpropyl group, and preferably a hydroxy C1-6 alkyl group;

Alkoxyalkyl groups such as a methoxymethyl group, an ethoxymethyl group, a 2-methoxyethyl group, a 2-ethoxyethyl group, a methoxy n-propyl group, an n-propoxymethyl group, an i-propoxyethyl group, an s-butoxymethyl group, a t-butoxyethyl group, a 2,2-dimethoxyethyl group, and a 2,2-dimethoxy-1,1-dimethylethyl group, and preferably a C1-6 alkoxy C1-6 alkyl group;

Acyloxyalkyl groups such as a formyloxymethyl group, a cetoxymethyl group, a 2-acetoxyethyl group, a propionyloxymethyl group, and a propionyloxyethyl group, and preferably a C1-7 acyloxy C1-6 alkyl group;

Acylalkyl groups such as a formylmethyl group, a 2-formylethyl group, a 3-formylpropyl group, a 1-formyl-1-methylethyl group, a 2-formyl-1,1-dimethylethyl group, an acetylmethyl group, a 2-acetylethyl group, a 3-acetylpropyl group, a 1-acetyl-1-methylethyl group, and a 2-acetyl-1,1-dimethylethyl group, and preferably a C1-7 acyl C1-6 alkyl group;

Carboxyalkyl groups such as a carboxymethyl group, a 2-carboxyethyl group, a 3-carboxypropyl group, a 1-carboxy-1-methylethyl group, and a 2-carboxy-1,1-dimethylethyl group, and preferably carboxy C1-6 alkyl group; and Alkoxycarbonyl alkyl groups such as a methoxycarbonyl methyl group, a 2-methoxycarbonyl ethyl group, a 3-methoxycarbonyl propyl group, a 1-methoxycarbonyl-1-methylethyl group, and a 2-methoxycarbonyl-1,1-dimethylethyl group, and preferably a C1-6 alkoxycarbonyl C1-6 alkyl group.

Examples of the "C1-8 alkylcarbonyl group which has a substituent" include C1-8 haloalkylcarbonyl groups such as a monofluoroacetyl group, a monochloroacetyl group, a monobromoacetyl group, a difluoroacetyl group, a dichloroacetyl group, a dibromoacetyl group, a trifluoroacetyl group, a trichloroacetyl group, a tribromoacetyl group, a 3,3,3-trifluoropropionyl group, a 3,3,3-trichloropropionyl group, and a 2,2,3,3,3-pentafluoropropionyl group.

The "C3-8 cycloalkylcarbonyl group" is a group obtained by bonding between a C3-8 cycloalkyl group and a carbonyl group.

The "C3-8 cycloalkyl group" which is bonded to a carbonyl group is an alkyl group configured of 3 to 8 carbon atoms having a cyclic portion. Examples of the "C3-8 cycloalkyl group" include a cyclopropyl group, a cyclobutyl group, a cyclopentyl group, a cyclohexyl group, a cycloheptyl group, and a cyclooctyl group. Among these, the C3-6 cycloalkyl group is preferable.

As the "C3-8 cycloalkyl group which has a substituent" which is bonded to a carbonyl group, alkyl-substituted cycloalkyl groups such as a 2,3,3-trimethyl cyclobutyl group, a 4,4,6,6-tetramethyl cyclohexyl group, and a 1,3-dibutyl cyclohexyl group, and preferably C3-6 cycloalkyl groups in which 1 to 3 C1-6 alkyl groups are substituted can be exemplified.

The "C6-10 arylcarbonyl group" is a group obtained by bonding between a C6-10 aryl group and a carbonyl group.

The "C6-10 aryl group" which is bonded to a carbonyl group is a monocyclic or polycyclic aryl group having 6 to 10 carbon atoms. Moreover, in the polycyclic aryl group, if at least one ring is an aromatic ring, the remaining rings may be any of a saturated alicycle, an unsaturated alicycle, or an aromatic ring. Examples of the C6-10 aryl group include a phenyl group, a naphthyl group, an azulenyl group, an indenyl group, an indanyl group, and a tetralinyl group. Among these, a phenyl group is preferable.

Examples of the "C6-10 aryl group which has a substituent" which is bonded to a carbonyl group include alkyl-substituted aryl groups, halogeno-substituted aryl groups, and alkoxy-substituted aryl groups such as a 2-chlorophenyl group, a 3,5-dichlorophenyl group, a 4-fluorophenyl group, a 3,5-difluorophenyl group, a 4-trifluoromethylphenyl group, and a 2-methoxy-1-naphthyl group. Among these, a C1-6 alkyl-substituted C6-10 aryl group, a halogeno-substituted C6-10 aryl group, and a C1-6 alkoxy-substituted aryl group are preferable.

The "5 to 10-membered heterocyclic carbonyl group" is a group obtained by bonding between a 5 to 10-membered heterocyclic group and a carbonyl group.

The "5 to 10-membered heterocyclic group" which is bonded to a carbonyl group is a 5 to 10-membered heterocyclic group including 1 to 4 hetero atoms selected from a nitrogen atom, an oxygen atom, and a sulfur atom as a configuration atom of a ring. The heterocyclic group may be monocyclic or polycyclic.

Examples of the heterocyclic group include a 5-membered heteroaryl group, a 6-membered heteroaryl group, a condensed heteroaryl group, a saturated heterocyclic group, and a partially unsaturated heterocyclic group.

Examples of the 5-membered heteroaryl group include pyrrolyl groups such as a pyrrol-1-yl group, a pyrrol-2-yl group, and a pyrrol-3-yl group; furyl groups such as a furan-2-yl group and a furan-3-yl group; thienyl groups such as a thiophen-2-yl group and a thiophen-3-yl group; imidazolyl groups such as an imidazol-1-yl group, an imidazol-2-yl group, an imidazol-4-yl group, and an imidazol-5-yl group; pyrazolyl groups such as a pyrazol-1-yl group, a pyrazol-3-yl group, a pyrazole-4-yl group, and pyrazol-5-yl group; oxazolyl groups such as an oxazol-2-yl group, an oxazol-4-yl group, and an oxazol-5-yl group; isoxazolyl groups such as an isoxazol-3-yl group, an isoxazol-4-yl group, and an isoxazol-5-yl group; thiazolyl groups such as a thiazol-2-yl group, a thiazol-4-yl, and a thiazol-5-yl group; isothiazolyl groups such as an isothiazol-3-yl group, an isothiazol-4-yl group, and an isothiazol-5-yl group; triazolyl groups such as a 1,2,3-triazol-1-yl group, a 1,2,3-triazol-4-yl group, a 1,2,3-triazol-5-yl group, a 1,2,4-triazol-1-yl group, 1,2,4-triazol-3-yl group, and 1,2,4-triazol-5-yl group; oxadiazolyl groups such as a 1,2,4-oxadiazol-3-yl group, a 1,2,4-oxadiazol-5-yl group, and a 1,3,4-oxadiazol-2-yl group; thiadiazolyl groups such as a 1,2,4-thiadiazol-3-yl group, a 1,2,4-thiadiazol-5-yl group, and a 1,3,4-thiadiazol-2-yl group; and tetrazolyl groups such as a tetrazol-1-yl group and a tetrazole-2-yl group;

Examples of the 6-membered heteroaryl group include pyridyl groups such as a pyridin-2-yl group, a pyridin-3-yl group, and a pyridin-4-yl group; pyrazinyl groups such as a pyrazin-2-yl group and a pyrazin-3-yl group; pyrimidinyl groups such as a pyrimidin-2-yl group, a pyrimidin-4-yl group, and a pyrimidin-5-yl group; pyridazinyl groups such as a pyridazin-3-yl group and a pyridazin-4-yl group; and a triazinyl group.

Examples of the condensed heteroaryl group include an indol-1-yl group, an indol-2-yl group, an indol-3-yl group, an indol-4-yl group, and indol-5-yl group, and indol-6-yl group, and an indol-7-yl group; a benzofuran-2-yl group, a benzofuran-3-yl group, a benzofuran-4-yl group, a benzofuran-5-yl group, a benzofuran-6-yl group, and a benzofuran-7-yl group; a benzothiophen-2-yl group, a benzothiophen-3-yl group, a benzothiophen-4-yl group, a benzothiophen-5-yl group, a benzothiophen-6-yl group, and a benzothiophen-7-yl group; a benzimidazol-1-yl group, a benzimidazol-2-yl group, a benzimidazol-4-yl group, a benzimidazol-5-yl group, a benzoxazol-2-yl group, a benzoxazol-4-yl group, a benzoxazol-5-yl group, a benzothiazol-2-yl group, a benzothiazol-4-yl group, and a benzothiazol-5-yl group; and a quinolin-2-yl group, a quinolin-3-yl group, a quinolin-4-yl group, a quinolin-5-yl group, a quinolin-6-yl group, a quinolin-7-yl group, and a quinolin-8-yl group.

Examples of other heterocyclic groups include groups in which one hydrogen atom is removed from a 5-membered saturated heterocycle such as a pyrrolidin-1-yl group, a pyrrolidin-2-yl group, a pyrrolidin-3-yl group, a tetrahydrofuran-2-yl group, a tetrahydrofuran-3-yl group, and a [1,3]dioxiran-2-yl group; groups in which one hydrogen atom is removed from a 6-membered saturated heterocycle such as a piperidin-1-yl group, a piperidin-2-yl group, a piperidin-3-yl group, a piperidin-4-yl group, a piperazin-1-yl group, a piperazin-2-yl group, a morpholin-2-yl group, a morpholin-3-yl group, and a morpholin-4-yl group; a 1,3-benzodioxol-4-yl group, a 1,3-benzodioxol-5-yl group, a 1,4-benzodioxan-5-yl group, a 1,4-benzodioxan-6-yl group, a 3,4-dihydro-2H-1,5-benzodioxepin-6-yl group, a 3,4-dihydro-2H-1,5-benzodioxepin-7-yl group, a 2,3-dihydrobenzofuran-4-yl group, a 2,3-dihydrobenzofuran-5-yl group, a 2,3-dihydrobenzofuran-6-yl group, and a 2,3-dihydrobenzofuran-7-yl group.

Examples of the "5-10 membered heterocyclic group which has a substituent" which is bonded to a carbonyl group include a 4-chloro-2-pyridinyl group, a 3-chloro-2-pyrazinyl group, a 4-methyl-2-pyridinyl group, a 5-trifluoromethyl-2-pyrimidinyl group, and a 3-methyl-2-quinolyl group.

The "C3-8 cycloalkyl C1-6 alkylcarbonyl group" is a group obtained by bonding between a C3-8 cycloalkyl group and a C1-6 alkylcarbonyl group.

As the "C3-8 cycloalkyl group" and the "C3-8 cycloalkyl group which has a substituent" which are bonded to the C1-6 alkylcarbonyl groups which are unsubstituted or have substituents, the same groups as the "C3-8 cycloalkyl group" and the "C3-8 cycloalkyl group which has a substituent" mentioned in the description of the "C3-8 cycloalkylcarbonyl group" can be exemplified, respectively. In addition, as the "C1-6 alkylcarbonyl group" and the "C1-6 alkylcarbonyl group which has a substituent", the same groups as the "alkylcarbonyl group" and the "alkylcarbonyl group which has a substituent" of C1-6 among groups mentioned in the description of the "C1-8 alkylcarbonyl group" can be exemplified, respectively.

The "C6-10 aryl C1-6 alkylcarbonyl group" is a group obtained by bonding between a C6-10 aryl group and a C1-6 alkylcarbonyl group.

As the "C6-10 aryl group" and the "C6-10 aryl group which has a substituent" which are bonded to the C1-6 alkylcarbonyl groups which are unsubstituted or have substituents, the same groups as the "C6-10 aryl group" and the "C6-10 aryl group which has a substituent" mentioned in the description of the "C6-10 arylcarbonyl group" can be exemplified, respectively. In addition, as the "C1-6 alkylcarbonyl group" and the "C1-6 alkylcarbonyl group which has a substituent", the same groups as the "alkylcarbonyl group" and the "alkylcarbonyl group which has a substituent" of C1-6 among groups mentioned in the description of the "C1-8 alkylcarbonyl group" can be exemplified, respectively.

The "5 to 10-membered heterocyclic C1-6 alkylcarbonyl group" is a group obtained by bonding between a 5 to 10-membered heterocyclic group and a C1-6 alkylcarbonyl group.

As the "5 to 10-membered heterocyclic group" and the "5 to 10-membered heterocyclic group which has a substituent" which are bonded to the C1-6 alkylcarbonyl groups which are unsubstituted or have substituents, the same groups as the "5 to 10-membered heterocyclic group" and the "5 to 10-membered heterocyclic group which has a substituent" mentioned in the description of the "5 to 10-membered heterocyclic carbonyl group" can be exemplified, respectively. In addition, as the "C1-6 alkylcarbonyl group" and the "C1-6 alkylcarbonyl group which has a substituent", the same groups as the "alkylcarbonyl group" and the "alkylcarbonyl group which has a substituent" of C1-6 among groups mentioned in the description of the "C1-8 alkylcarbonyl group" can be exemplified, respectively.

The "C1-8 alkyloxycarbonyl group" is a group obtained by bonding between a C1-8 alkoxy group and a carbonyl group.

Examples of the "C1-8 alkoxy group" which is bonded to a carbonyl group include a methoxy group, an ethoxy group, an n-propoxy group, an i-propoxy group, an n-butoxy group, an i-butoxy group, an s-butoxy group, a t-butoxy group, an n-pentyloxy group, an i-pentyloxy group, a 2-methylbutoxy group, a neopentyl group, and an n-hexyloxy group.

Examples of the "C1-8 alkyloxycarbonyl group" include a methoxycarbonyl group, an ethoxycarbonyl group, an n-propoxycarbonyl group, an i-propoxycarbonyl group, an n-butoxycarbonyl group, an i-butoxycarbonyl group, a t-butoxycarbonyl group, an n-pentyloxycarbonyl group, and an n-hexyloxycarbonyl group.

Examples of the "C1-8 alkoxy group which has a substituent" which is bonded to a carbonyl group include C1-8 haloalkoxy groups such as a fluoromethoxy group, a chloromethoxy group, a bromomethoxy group, a difluoromethoxy group, a dichloromethoxy group, a dibromomethoxy group, a trifluoromethoxy group, a trichloromethoxy group, a tribromometoxy group, a 2,2,2-trifluoroethoxy group, a 2,2,2-trichloroethoxy group, a pentafluoroethoxy group, a 4-fluorobutoxy group, a 3,3,3-trifluoropropoxy group, a 2,2,2-trifluoro-1-trifluoromethylethoxy group, and a perfluorohexyloxy group; hydroxy C1-8 alkoxy groups such as a 2-hydroxyethoxy group and a 2-hydroxypropoxy group; C1-6 alkoxy C1-8 alkoxy groups such as a methoxymethoxy group, a 1-methoxyethoxy group, a 2-methoxyethoxy group, an ethoxymethoxy group, a 1-ethoxyethoxy group, a 2-ethoxyethoxy group, a 1-methoxy-n-propoxy group, a 2-methoxy-n-propoxy group, and a 3-methoxy-n-propoxy group; C3-8 cycloalkyl C1-8 alkoxy groups such as a cyclopropylmethoxy group, a cyclobutylmethoxy group, a cyclopentylmethoxy group, a cyclohexylmethoxy group, a 2-methylcyclopropylmethoxy group, a 2,3-dimethylcyclopropylmethoxy group, and a 2-cyclopropylethoxy group; C7-11 aralkyloxy groups such as a benzyloxy group and a phenethyloxy group; C1-7 acyl C1-8 alkoxy groups such as an acetylmethoxy group and a 2-acetylethoxy group; cyano C1-8 alkoxy groups such as a cyanomethoxy group and a 2-cyanoethoxy, and C3-8 cycloalkyl C1-8 alkoxy groups having a substituent such as a chlorocyclohexylmethoxy group, a bromocyclohexylmethoxy group, a 2-methylcyclopropylmethoxy group, a 2,3-dimethylcyclopropylmethoxy group, a spiro[2.2]penta-1-yl methoxy group, a 1-methyl-spiro[2.2]penta-1-yl methoxy group, a 1-hydroxymethyl spiro[2.2]penta-1-yl methoxy group, a 4,4-difluoro-spiro[2.2]penta-1-yl methoxy group, or a bicyclopropyl-2-yl methoxy group.

Examples of the "C1-8 alkyloxycarbonyl group which has a substituent" include cycloalkylalkyloxycarbonyl groups such as a cyclopropylmethoxycarbonyl group, cycloalkenylalkyloxycarbonyl groups such as a cyclopentenylmethoxycarbonyl group, haloalkyloxycarbonyl groups such as a fluoromethoxycarbonyl group, aralkyloxycarbonyl groups such as a benzyloxycarbonyl group, heteroarylalkyloxycarbonyl groups such as a 2-pyridylmethoxycarbonyl group, and hydroxyalkyloxycarbonyl groups such as a hydroxymethoxycarbonyl group.

The "C3-8 cycloalkyloxycarbonyl group" is a group obtained by bonding between a C3-8 cycloalkoxy group and a carbonyl group.

Examples of the "C3-8 cycloalkoxy group" which is bonded to a carbonyl group include a cyclopropyloxy group, a cyclobutyloxy group, a cyclopentyloxy group, a cyclohexyloxy group, and a cycloheptyloxy group.

Examples of the "C3-8 cycloalkoxy group which has a substituent" include a chlorocyclohexyloxy group, a bromocyclohexyloxy group, a 2-methylcyclopropyloxy group, a 2,3-dimethylcyclopropyloxy group, a spiro[2.2]penta-1-yloxy group, a 1-methyl-spiro[2.2]penta-1-yloxy group, a 1-hydroxymethyl spiro[2.2]penta-1-yloxy group, a 4,4-difluoro-spiro[2.2]penta-1-yloxy group, and a bicyclopropyl-2-yloxy group.

The "C6-10 aryloxycarbonyl group" is a group obtained by bonding between a C6-10 aryloxy group and a carbonyl group.

As the "C6-10 aryl group" and the "C6-10 aryl group which has a substituent" configuring the C6-10 aryloxy group, the same groups as the "C6-10 aryl group" and the "C6-10 aryl group which has a substituent" mentioned in the description of the "C6-10 arylcarbonyl group" can be exemplified, respectively.

Examples of the "C6-10 aryloxycarbonyl group" include a phenyloxycarbonyl group and a naphthoxycarbonyl group.

The "5 to 10-membered heterocyclic oxycarbonyl group" is a group obtained by bonding between a 5 to 10-membered heterocyclicoxy group and a carbonyl group.

As the "5 to 10-membered heterocyclic group" and the "5 to 10-membered heterocyclic group configuring the 5 to 10-membered heterocyclic oxycarbonyl group, the same groups as the "5 to 10-membered heterocyclic group" and the "5 to 10-membered heterocyclic group which has a substituent" mentioned in the description of the "5 to 10-membered heterocyclic carbonyl group" can be exemplified, respectively.

The "C1-8 alkylthiocarbonyl group" is a group obtained by bonding between a C1-8 alkyl group and a thiocarbonyl group.

As the "C1-8 alkyl group" and the "C1-8 alkyl group which has a substituent" which are bonded to thiocarbonyl groups, the same groups as the "C1-8 alkyl group" and the "C1-8 alkyl group which has a substituent" mentioned in the description of the "C1-8 alkylcarbonyl group" can be exemplified, respectively.

Examples of the "C1-8 alkylthiocarbonyl group" include a methylthiocarbonyl group, an ethylthiocarbonyl group, an n-propylthiocarbonyl group, an isopropylthiocarbonyl group, an n-butylthiocarbonyl group, an iso-butylthiocarbonyl group, an s-butyhhiocarbonyl group, and a t-butylthiocarbonyl group.

The "di C1-8 alkyl sulfamoyl group" is a group obtained by bonding between two C1-8 alkyl groups and a sulfamoyl group at an N-position.

As the "C1-8 alkyl group" and the "C1-8 alkyl group which has a substituent" which are bonded to sulfamoyl groups, the same groups as the "C1-8 alkyl group" and the "C1-8 alkyl group which has a substituent" mentioned in the description of the "C1-8 alkylcarbonyl group" can be exemplified, respectively. The two C1-8 alkyl groups may be the same as or different from each other.

Examples of the "di C1-8 alkylsulfamoyl group" include an N,N-dimethylsulfamoyl group and an N,N-diethyl sulfamoyl group.

The "C1-8 alkylsulfonyl group" is a group obtained by bonding between a C1-8 alkyl group and a sulfonyl group.

As the "C1-8 alkyl group" and the "C1-8 alkyl group which has a substituent" which are bonded to sulfonyl groups, the same groups as the "C1-8 alkyl group" and the "C1-8 alkyl group which has a substituent" mentioned in the description of the "C1-8 alkylcarbonyl group" can be exemplified, respectively.

Examples of the "C1-8 alkylsulfonyl group" include a methylsulfonyl group, an ethylsulfonyl group, an n-propylsulfonyl group, an i-propylsulfonyl group, an n-butylsulfonyl group, an i-butylsulfonyl group, an s-butylsulfonyl group, a t-butylsulfonyl group, an n-pentylsulfonyl group, an i-pentylsulfonyl group, a neopentylsulfonyl group, a 1-ethylpropylsulfonyl group, an n-hexylsulfonyl group, and an i-hexylsulfonyl group.

Examples of the "C1-8 alkylsulfonyl group which has a substituent" include haloalkylsulfonyl groups such as a trifluoromethylsulfonyl group and aralkylsulfonyl groups such as a benzylsulfonyl group.

The "C3-8 cycloalkylsulfonyl group" is a group obtained by bonding between a C3-8 cycloalkyl group and a sulfonyl group.

As the "C3-8 cycloalkyl group" and the "C3-8 cycloalkyl group which has a substituent" which are bonded to sulfonyl groups which are unsubstituted or have substituents, the same groups as the "C3-8 cycloalkyl group" and the "C3-8 cycloalkyl group which has a substituent" mentioned in the description of the "C3-8 cycloalkylcarbonyl group" can be exemplified, respectively.

The "C6-10 arylsulfonyl group" is a group obtained by bonding between a C6-10 aryl group and a sulfonyl group.

As the "C6-10 aryl group" and the "C6-10 aryl group which has a substituent" which are bonded to sulfonyl groups, the same groups as the "C6-10 aryl group" and the "C6-10 aryl group which has a substituent" mentioned in the description of the "C6-10 arylcarbonyl group" can be exemplified, respectively.

Examples of the "C6-10 arylsulfonyl group" include a phenylsulfonyl group.

Examples of the "C6-10 arylsulfonyl group which has a substituent" include a 4-methylphenylsulfonyl group.

The "5 to 10-membered heterocyclic sulfonyl group" is a group obtained by bonding between a 5 to 10-membered heterocyclic group and a sulfonyl group.

As the "5 to 10-membered heterocyclic group" and the "5 to 10-membered heterocyclic group which has a substituent" which are bonded to sulfonyl groups, the same groups as the "5 to 10-membered heterocyclic group" and the "5 to 10-membered heterocyclic group which has a substituent" mentioned in the description of the "5 to 10-membered heterocyclic carbonyl group" can be exemplified, respectively.

[$R^2$]

$R^2$ represents a hydrogen atom, a C1-8 alkyl group which is unsubstituted or has a substituent, or a C1-8 alkylcarbonyl group which is unsubstituted or has a substituent.

As the "C1-8 alkyl group which is unsubstituted or has a substituent" in $R^2$, the same groups as the "C1-8 alkyl group" and the "C1-8 alkyl group which has a substituent" mentioned in the description of the "C1-8 alkylcarbonyl group" in $R^1$ can be exemplified. In addition, as the "C1-8 alkylcarbonyl group which is unsubstituted or has a substituent", the same groups as the "C1-8 alkylcarbonyl group" and the "C1-8 alkylcarbonyl group which has a substituent" mentioned in the description of the "C1-8 alkylcarbonyl group" in $R^1$ can be exemplified. Among these, $R^2$ is preferably a hydrogen atom.

[$R^3$, $R^4$, and $R^5$]

Each of $R^3$, $R^4$, and $R^5$ independently represents a hydrogen atom, a C1-8 alkyl group which is unsubstituted or has a substituent, or a halogen atom.

Among these, $R^3$ is preferably a hydrogen atom, or a C1-8 alkyl group which is unsubstituted or has a substituent.

As the "C1-8 alkyl group which is unsubstituted or has a substituent" in $R^3$, $R^4$, and $R^5$, the same groups as the "C1-8 alkyl group" and the "C1-8 alkyl group which has a substituent" mentioned in the description of the "C1-8 alkylcarbonyl group" in $R^1$ can be exemplified.

[E]

E represents a furyl group, a pyrrolyl group, a tetrazolyl group, a thiazolyl group, a pyrazolyl group, a phenyl group, or a pyridyl group. Specifically, E is any one of a 2-furyl group, a 3-furyl group, a 2-pyrrolyl group, a 3-pyrrolyl group, a 1-tetrazolyl group, a 5-tetrazolyl group, a 2-thiazolyl group, a 4-thiazolyl group, a 5-thiazolyl group, a 1-pyrazolyl group, a 3-pyrazolyl group, a 4-pyrazolyl group, a 5-pyrazolyl group, a phenyl group, a 2-pyridyl group, 3-pyridyl group, and a 4-pyridyl group.

Among these, E is preferably a phenyl group. In a case where E is a phenyl group, $R^2$ is preferably a hydrogen atom.

E may be a group which is unsubstituted or has a substituent. In a case where E has a substituent, the substituent is represented by A.

[A and n]

A represents a halogen atom, a cyano group, a C1-8 alkyl group which is unsubstituted or has a substituent, a C1-8 alkoxy group which is unsubstituted or has a substituent, a C3-8 cycloalkyl group which is unsubstituted or has a substituent, a C3-8 cycloalkoxy group which is unsubstituted or has a substituent, a C6-10 aryl group which is unsubstituted or has a substituent, a C6-10 aryloxy group which is unsubstituted or has a substituent, a 5 to 10-membered heterocyclic group which is unsubstituted or has a substituent, or a 5 to 10 membered heterocyclyloxy group which is unsubstituted or has a substituent.

As the "C1-8 alkyl group which is unsubstituted or has a substituent" in A, the same groups as the "C1-8 alkyl group" and the "C1-8 alkyl group which has a substituent" mentioned in the description of the "C1-8 alkylcarbonyl group" in $R^1$ can be exemplified.

As the "C1-8 alkoxy group which is unsubstituted or has a substituent" in A, the same groups as the "C1-8 alkoxy group" and the "C1-8 alkoxy group which has a substituent" mentioned in the description of the "C1-8 alkyloxy carbonyl group" in $R^1$ can be exemplified.

As the "C3-8 cycloalkoxy group which is unsubstituted or has a substituent" in A, the same groups as the "C3-8 cycloalkyl group" and the "C3-8 cycloalkyl group which has a substituent" mentioned in the description of the "C3-8 cycloalkylcarbonyl group" in $R^1$ can be exemplified.

As the "C3-8 cycloalkoxy group which is unsubstituted or has a substituent" in A, the same groups as the "C3-8 cycloalkoxy group" and the "C3-8 cycloalkoxy group which has a substituent" mentioned in the description of the "C3-8 cycloalkyloxy carbonyl group" in $R^1$ can be exemplified.

As the "C6-10 aryl group which is unsubstituted or has a substituent" in A, the same groups as the "C6-10 aryl group" and the "C6-10 aryl group which has a substituent" mentioned in the description of the "C6-10 arylcarbonyl group" in $R^1$ can be exemplified.

As the "C6-10 aryloxy group which is unsubstituted or has a substituent" in A, a group obtained by bonding between the "C6-10 aryl group" and an oxy group and a group obtained by bonding between the "C6-10 aryl group which has a substituent" and an oxy group mentioned in the description of the "C6-10 arylcarbonyl group" in $R^1$ can be exemplified.

As the "5 to 10-membered heterocyclic group which is unsubstituted or has a substituent" in A, the same groups as the "5 to 10-membered heterocyclic group" and the "5 to 10-membered heterocyclic group which has a substituent" mentioned in the description of the "5 to 10-membered heterocyclic carbonyl group" in $R^1$ can be exemplified.

The "5 to 10-membered heterocyclyloxy group" is a group obtained by bonding between a 5 to 10-membered heterocyclic group and an oxy group.

As the "5 to 10-membered heterocyclic group" and the "5 to 10-membered heterocyclic group which has a substituent" which are bonded to oxy groups, the same groups as the "5 to 10-membered heterocyclic group" and the "5 to 10-membered heterocyclic group which has a substituent" mentioned in the description of the "5 to 10-membered heterocyclic carbonyl group" can be exemplified, respectively.

Examples of the "5 to 10-membered heterocyclyloxy group" include a pyridyloxy group and a pyridazinyloxy group.

Among these, A is preferably any one of a cyano group, the C1-8 alkyl group which is unsubstituted or has a substituent, the C1-8 alkoxy group which is unsubstituted or has a substituent, a phenyl group which is unsubstituted or has a substituent, a phenoxy group which is unsubstituted or has a substituent, the 5 to 6-membered heteroaryl group which is unsubstituted or has a substituent, or the 5 to 6-membered heteroaryloxy group which is unsubstituted or has a substituent.

n represents the number of A, and is any integer of 0 to 5. Among these, n is preferably any integer of 1 to 5.

When n is equal to or greater than 2, A's may be the same as or different from each other.

In the pyridine compound according to the present invention, a hydrate, various solvates, a crystal polymorphism substance, or the like is included. Furthermore, the pyridine compound according to the present invention contains stereoisomers based on asymmetric carbon atoms or a double bond or a mixture of these.

The pyridine compound according to the present invention may be a salt. The salt of the pyridine compound is not particularly limited as long as it is an agriculturally acceptable salt. Examples of the salt include salts of inorganic acids such as hydrochloric acid and sulfuric acid; salts of organic acids such as acetic acid and lactic acid; salts of alkali metals such as lithium, sodium, and potassium; salts of alkaline earth metals such as calcium and magnesium; salts of transition metals such as iron and copper; and salts of organic bases such as ammonia, triethylamine, tributylamine, pyridine, and hydrazine.

[Production Method of Compound According to the Invention]

The compound according to the present invention can be produced, for example, using the known method described in PTL 3 or the like. For example, in a case where $R^1$ of the formula (1) is a group having a carbonyl group (—C(=O)—) at a terminal to be bonded to a nitrogen atom (N), the compound of the present invention can be produced by the following synthetic method.

[Chem. 9]

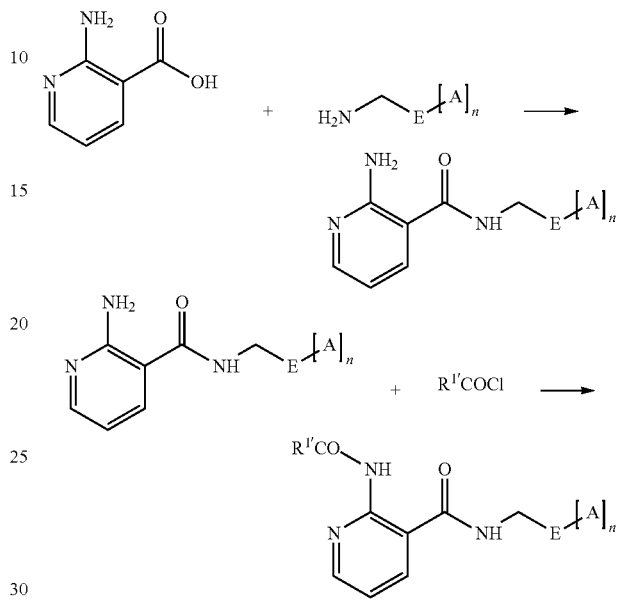

(In the formula, each of E, A, and n represents the same as E, A, and n described in the formula (1). $R^{1'}$ represents a group in which a terminal carbonyl group is removed from $R^1$ described in the formula (1).)

In any reaction, after the reaction is completed, it is possible to efficiently isolate the target product by performing a general post-treatment operation in synthetic organic chemistry and known separation and purification means in the related art as necessary.

The structure of the target product can be identified and confirmed by a measurement of $^1$H-NMR spectrum, IR spectrum, or mass spectrum, or elemental analysis or the like.

2) Agricultural Fungicide

The agricultural fungicide according to the present invention contains at least one selected from the pyridine compound represented by the formula (1) according to the present invention or salts thereof as an active ingredient.

The fungicide of the present invention has excellent fungicidal activity against wide variety of filamentous fungi, for example, fungi belonging to algal fungi (Oomycetes), (sac) fungi (Ascomycetes), imperfect fungi (Deuteromycetes), and basidiomycotina (Basidiomycetes).

The fungicide of the present invention can be used for controlling various diseases occurring when cultivating agricultural crops including flowers, lawn, and grass by a seed treatment, a foliage application, a soil application, a submerged application, or the like.

For example, the fungicide of the present invention can be used for controlling the following diseases.

Sugar beet: Brown spot (*Cercospora beticola*), black root rot (*Aphanomyces cochlloides*), root rot (*Thanatephorus cucumeris*), and leaf rot (*Thanatephorus cucumeris*);

Peanut: Brown spot (*Mycosphaerella arachidis*) and leaf spot (*Mycosphaerella berkeleyi*);

Cucumber: Powdery mildew (*Sphaerotheca fuliginea*), downy mildew (*Pseudoperonospora cubensis*), gummy stem blight (*Mycosphaerella melonis*), Fusarium wilt (*Fusarium oxysporum*), Sclerotinia rot (*Sclerotinia sclerotiorum*), gray mold (*Botrytis cinerea*), anthracnose (*Colletotrichum orbiculare*), scab (*Cladosporium cucumerinum*), brown spot (*Corynespora cassicola*), damping-off (*Pythium debaryanam, Rhizoctonia solani* Kuhn), and bacterial blight (*Pseudomonas syringae* pv. Lecrymans);

Tomato: Gray mold (*Botrytis cinerea*), leaf mold (*Cladosporium fulvum*), and late blight (*Phytophthora infestans*);

Eggplant: Gray mold (*Botrytis cinerea*), black blight (*Corynespora melongenae*), powdery mildew (*Erysiphe cichoracearum*), and susukabi disease (*Mycovellosiella nattrassii*);

Strawberry: Gray mold (*Botrytis cinerea*), powdery mildew (*Sohaerotheca humuli*), anthracnose (*Colletotrichum acutatum, Colletotrichum fragariae*), and late blight (*Phytophthora cactorum*);

Onion: Grey rot (*Botrytis allii*), gray mold (*Botrytis cinerea*), vitiligo leaf blight (*Botrytis squamosa*), and downy mildew (*Peronospora destructor*);

Cabbage: Clubroot (*Plasmodiophora brassicae*), soft rot (*Erwinia carotovora*), and downy mildew (*Peronospora parasitica*);

Kidney bean: Sclerotinia rot (*Sclerotinia sclerotiorum*) and gray mold (*Botrytis cinerea*);

Apple: Powdery mildew (*Podosphaera leucotricha*), scab (*Venturia inaequalis*), blossom blight (*Monilinia mali*), black spot (*Mycosphaerella pomi*), canker (*Valsa mali*), alternaria leaf spot (*Alternaria mali*), chocolate spot (*Gymnosporangium yamadae*), ring spot (*Botryosphaeria berengeriana*), anthracnose (*Glomerella cingulata, Colletotrichum acutatum*), brown spot (*Diplocarpon mali*), fly speck (*Zygophiala jamaicensis*), and sooty blotch (*Gloeodes pomigena*);

Kaki: Powdery mildew (*Phyllactinia kakicola*), anthracnose (*Gloeosporium kaki*), and angular leaf spot (*Cercospora kaki*);

Peach: Brown rot (*Monilinia fructicola*), scab (*Cladosporium carpophilum*), and phomopsis rot (*Phomopsis sp.*);

Cherry: Brown rot (*Monilinia fructicola*);

Grape: Gray mold (*Botrytis cinerea*), powdery mildew (*Uncinula necator*), ripe rot (*Glomerella cingulata, Colletotrichum acutatum*), downy mildew (*Plasmopara viticola*), anthracnose (*Elsinoe ampelina*), brown spot (*Pseudocercospora vitis*), and black rot (*Guignardia bidwellii*);

Pear: Scab (*Venturia nashicola*), chocolate spot (*Gymnosporangium asiaticum*), black spot (*Alternaria kikuchiana*), ring spot (*Botryosphaeria berengeriana*), and powdery mildew (*Phyllactinia mali*);

Tea: Gay blight (*Pestalotia theae*) and anthracnose (*Colletotrichum theae-sinensis*);

Citrus: Scab (*Elsinoe fawcetti*), blue mold (*Penicillium italicum*), green mold (*Penicillium digitatum*), gray mold (*Botrytis cinerea*), black spot (*Diaporthe citri*), and canker (*Xanthomonas campestris* pv. Citri);

Wheat: Powdery mildew (*Erysiphe graminis* f. sp. *tritici*), fusarium head blight (*Gibberella zeae*), rust (*Puccinia recondita*), brown snow rot (*Pythium iwayamai*), pink snow rot (*Monographella nivalis*), eye spot (*Pseudocercosporella herpotrichoides*), leaf blight (*Septoria tritici*), glume blotch (*Leptosphaeria nodorum*), typhula snow blight (*Typhula incamata*), sclerotial snow mold (*Myriosclerotinia borealis*), and damping-off (*Gaeumanomyces graminis*);

Barley: Leaf stripe (*Pyrenophora graminea*), leaf blotch (*Rhynchosporium secalis*), and loose smut (*Ustilago tritici, U. nuda*);

Rice: Blast (*Pyricularia oryzae*), sheath blight (*Rhizoctonia solani*), bakanae (*Gibberella fujikuroi*), brown spot (*Cochliobolus niyabeanus*), damping-off (*Pythium graminicolum*), bacterial leaf blight (*Xanthomonas oryzae*), pseudomonas glumae (*Burkholderia plantarii*), bacterial brown stripe (*Acidovorax avenae*), pseudomonas glumae (*Burkholderia glumae*);

Tobacco: Sclerotinia rot (*Sclerotinia sclerotiorum*) and powdery mildew (*Erysiphe cichoracearum*);

Tulip: gray mold (*Botrytis cinerea*);

Bentgrass: large-grain sclerotial snow mold (*Sclerotinia borealis*), pythium red blight (*Pythium aphanidermatum*), and anthracnose (*Colletotrichum graminicola*);

Orchard grass: Powdery mildew (*Erysiphe graminis*);

Soybean: Purple seed stain (*Cercospora kikuchii*), and downy mildew (*Peronospora Manshurica*), brown stem rot (*Phytophthora sojae*); and Potato-Tomato: Late blight (*Phytophthora infestans*).

In addition, the fungicide of the present invention also has excellent bactericidal effect against drug-resistant bacteria. Examples of the drug-resistant bacteria include gray mold fungi (*Botrytis cinerea*) and sugar beet brown spot fungi (*Cercospora beticola*) showing resistance to benzimidazole-based fungicides such as thiophanate methyl, benomyl, and carbendazim, apple scab fungi (Venturia *inaequalis*), and pear scab fungi (*Venturia nashicola*); and gray mold fungi (*Botrytis cinerea*) showing resistance to dicarboximide-based fungicides (for example, vinclozolin, procymidone, and iprodione).

Examples of diseases to which the fungicide of the present invention is more preferably applied include apple scab, cucumber gray mold, wheat powdery mildew, tomato late blight, wheat rust, rice blast, and cucumber wilt.

In addition, the fungicide of the present invention is a drug which exhibits little phytotoxicity, has low toxicity to fish or warm-blooded animals, and has high safe.

The fungicide of the present invention can be used as a form that can be made as an agrochemical, that is, a form of agrochemical formulation such as a wettable powder, granules, a dustable powder, an emulsifiable concentrate, a water soluble powder, a suspension concentrate (a suspo-emulsion, an emulsion), and water dispersible granule.

Examples of an additive and a carrier used in a solid formulation include vegetable powders such as soy flour and wheat flour, plaster, talc, bentonite, pyrophyllite, and clay, and organic and inorganic compounds such as sodium benzoate, urea, and sodium sulfate.

Examples of the solvent used in formulation of a liquid include kerosene, xylene, and petroleum-based aromatic hydrocarbon, cyclohexane, cyclohexanone, dimethylformamide, dimethylsulfoxide, alcohol, acetone, trichloroethylene, methylisobutyl ketone, mineral oil, vegetable oil, and water.

Furthermore, in order to make these formulations take a uniform and stable form, it is possible to add a surfactant as necessary.

The surfactant capable of being added is not particularly limited. Examples of the surfactant include nonionic surfactants such as alkyl phenyl ether in which polyoxyethylene is added, alkyl ether in which polyoxyethylene is added, higher fatty acid ester in which polyoxyethylene is added, sorbitan higher fatty acid ester in which polyoxyethylene is added, and tristyrylpheny ether in which polyoxyethylene is added, a sulfuric ester salt of alkyl phenyl ether in which polyoxyethylene is added, alkyl benzene sulfonate, a sulfuric acid ester salt of higher alcohol, alkyl naphthalene sulfonate, polycarboxylate, lignin sulfonate, a formaldehyde condensate of alkyl naphthalene sulfonate, and a isobutylene-maleic anhydride copolymer.

The fungicide of the present invention is used by a method of diluting the wettable powder, emulsifiable concentrate, suspension concentrate (suspo-emulsion, emulsion), water soluble powder, or water dispersible granule obtained in the above manner to a predetermined concentration with water to make a solution, suspension, or emulsion, and spraying the solution, suspension, or emulsion to plants. In addition, particle and granules are used by a method of spraying directly to plants.

Usually, the amount of active ingredient in the fungicide of the present invention is preferably 0.01% by mass to 90% by mass, and more preferably 0.05% by mass to 85% by mass with respect to the entirety of formulations.

Although the applying amount of the fungicide of the present invention varies depending on weather conditions, a formulation form, application time, an application method, an application site, a control target disease, or target crops, usually, the applying amount is 1 g to 1,000 g, and preferably 10 g to 100 g as the amount of active ingredient per hectare.

In a case of diluting the wettable powder, emulsifiable concentrate, suspension concentrate (suspo-emulsion, emulsion), water soluble power, or water dispersible granule with water, the applying concentration is 1 ppm to 1,000 ppm, and preferably 10 ppm to 250 ppm.

Other fungicides, insecticide-acaricides, nematicides, soil pesticides, anthelmintics, plant growth regulators, or synergists can be mixed to the fungicide of the present invention.

Representative examples of other fungicides, insecticide-acaricides, nematicides, soil pesticides, anthelmintics, plant growth regulators, or synergists which can be used by mixing are shown below.

Fungicide:

(1) Benzimidazole base: Benomyl, carbendazim, fuberidazole, thiabendazole, and thiophanate methyl;

(2) Dicarboxyimide base: Chlozolinate, iprodione, procymidone, and vinclozolin;

(3) DMI-fungicide base: Imazalil, oxopoconazole, pefurazoate, prochloraz, triflumizole, triforine, pyrifenox, fenarimol, nuarimol, azaconazole, bitertanol, bromuconazole, cyproconazole, difenoconazole, diniconazole, epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole, etaconazole, and furconazole-cis;

(4) Phenylamide base: Benalaxyl, furalaxyl, metalaxyl, metalaxyl-M, oxadixyl, and ofurace;

(5) Amine base: Aldimorph, dodemorph, fenpropimorph, tridemorph, fenpropidine, piperalin, and spiroxamine;

(6) Phosphorothiolate base: EDDP, iprobenfos, and pyrazophos;

(7) Dithiolane base: Isoprothiolane;

(8) Carboxamide: Benodanil, boscalid, carboxin, fen franc, flutolanil, furametpyr, mepronil, oxycarboxin, penthiopyrad, thifluzamide, bixafen, isopyrazam, penflufen, fluxapyroxad, and sedaxane;

(9) Hydroxy-(2-amino)pyrimidine base: Bupirimate, dimethirimol, and ethirimol;

(10) AP fungicide (anilinopyrimidine) base: Cyprodinil, mepanipyrim, and pyrimethanil;

(11) N-phenyl carbamate base: Diethofencarb;

(12) QoI-fungicide (Qo inhibitor) base: Azoxystrobin, picoxystrobin, pyraclostrobin, kresoxim-methyl, trifloxystrobin, dimoxystrobin, metominostrobin, orysastrobin, famoxadone, fluoxastrobin, fenamidone, and metominofen;

(13) PP fungicide (phenylpyrrole) base: Fenpiclonil, fludioxonil, and the like;

(14) Quinoline base: Quinoxyfen;

(15) AH fungicide (aromatic hydrocarbon) base: Biphenyl, chloroneb, dichloran, quintozene, tecazene, and torquephosmethyl;

(16) MBI-R base: Fthalide, pyroquilon, and tricyclazole;

(17) MBI-D base: Carpropamid, diclocymet, and fenoxanil;

(18) SBI agent: Fenhexamid, pyributicarb, and tabinafin;

(19) Phenyl urea: Pencycuron;

(20) QiI-fungicide (Qi inhibitor): Cyazofamid and amisulbrom;

(21) Benzamide base: Zoxamide;

(22) Enopyranuron base: Blasticidin and mildiomycin;

(23) Hexopyranosyl base: Kasugamycin;

(24) Glucopyranosyl base: Streptomycin and validamycin;

(25) Cyanoacetamide base: Cymoxanil;

(26) Carbamate base: Iodocarb, propamocarb, prothiocarb, and polycarbamate;

(27) Uncoupling agent: Binapacryl, dinocap, ferimzone, and fluazinam;

(28) Organotin compound: Fentin acetate, triphenyltin chloride, and triphenyltin hydroxide;

(29) Phosphoric acid ester: Phosphorous acid, tolclofos-methyl, and fosetyl;

(30) Phthalamic acid base: Tecloftalam;

(31) Benzotriazine base: Triazoxide;

(32) Benzene sulfonamide base: Flusulfamide;

(33) Pyridazinone: Diclomezine;

(34) CAA fungicide (carboxylic acid amide) base: Dimethomorph, flumorph, benthiavalicarb, iprovalicarb, and mandipropamid;

(35) Tetracycline: Oxytetracycline;

(36) Thiocarbamate base: Methasulfocarb;

(37) Other compounds: Etridiazole, polyoxin, oxolinic acid, hydroxy isoxazole, hydroxyisoxazole, octhilinone, silthiofam, diflumetorim, acibenzolar S methyl, probenazole, tiadinil, ethaboxam, cyflufenamide, proquinazid, metrafenone, fluopicolide, cupric hydroxide, organocopper, sulfur, ferbam, mancozeb, maneb, metiram, propineb, thiuram, zineb, ziram, captan, captafol, folpet, chlorothalonil, dichlofluanid, tolylfluanid, dodine, guazatine, iminoctadine acetate, iminoctadine docecyl benzene sulfonate, anilazine, dithianon, chloropicrin, aazomet, quinomethionate, cyprofuram, silthiofam, agrobacterium, and fluoroimide);

Insecticide-acaricide, nematicide, soil pesticide, and anthelmintic:

(1) Organo(thio)phosphate base: Acephate, azamethiphos, azinphos-methyl, azinphos-ethyl, bromophos-ethyl, bromfenvinphos, BRP, chlorpyrifos, chlorpyrifos-methyl, chlorpyrifos-ethyl, chlorfenvinphos, cadusafos, carbophenothion, chlorethoxyfos, chlormephos, coumaphos, cyanofenphos, cyanophos, CYAP, diazinon, dichlorvos, dicrotophos, dimethoate, disulfoton, demeton-S-methyl, dimethylvinphos, demeton-S-methylsulfone, dialifos, diazinon, dichlofenthion, dioxabenzophos, disulfoton, ethion, ethoprophos, etrimfos, EPN, fenamiphos, fenitrothion, fenthion, fensulfothion, flupyrazofos, fonofos, formothion, fosmethilan, heptenophos, isazophos, iodofenphos, isofenphos, isoxathion, iprobenfos, malathion, mevinphos, methamidophos, methidathion, monocrotophos, mecarbam, methacrifos, naled, omethoate, oxydemeton-methyl, paraoxon, parathion, parathion-methyl, phenthoate, phosalone, phosmet, phosphamidon, phorate, phoxim, pirimiphos-methyl, pirimiphos-ethyl, profenofos, prothiofos, fosthiazate, phosphocarb, propaphos, propetamphos, prothoate, pyridaphenthion, pyraclofos, quinalphos, salithion, sulprofos, sulfotep, tetrachlorvinphos, terbufos, triazophos, trichlorfon, tebupirimfos, temephos, thiometon, and vamidothion;

(2) Carbamate base: Alanycarb, aldicarb, bendiocarb, benfuracarb, carbaryl, carbofuran, carbosulfan, fenoxycarb, fenothiocarb, methiocarb, methomyl, oxamyl, pirimicarb, propoxur, thiodicarb, triazamate, ethiofencarb, fenobucarb, MIPC, MPMC, MTMC, pyridaphenthion, furathiocarb, XMC, aldoxycarb, allyxycarb, aminocarb, bendiocarb, bufencarb, butacarb, butocarboxim, butoxycarboxim, cloethocarb, dimetilan, formetanate, isoprocarb, metam-sodium, metolcarb, promecarb, thiofanox, trimethacarb, and xylylcarb;

(3) Pyrethroid base: Allethrin, bifenthrin, cyfluthrin, beta-cyfluthrin, cyhalothrin, lambda-cyhalothrin, cyphenothrin, cypermethrin, alpha-cypermethrin, beta-cypermethrin, zeta-cypermethrin, deltamethrin, esfenvalerate, ethofenprox, fenpropathrin, fenvalerate, imiprothrin, permethrin, prallethrin, pyrethrin, pyrethrin I, pyrethrin II, resmethrin, silafluofen, fluvalinate, tefluthrin, tetramethrin, tralomethrin, transfluthrin, profluthrin, dimefluthrin, acrinathrin, cycloprothrin, halfenprox, flucythrinate, bioallethrin, bioethanomethrin, biopermethrin, bioresmethrin, trans permethrin, empenthrin, fenfluthrin, fenpyrithrin, flubrocythrinate, flufenprox, flumethrin, metofluthrin, phenothrin, protrifenbute, piresmethrin, and terallethrin;

(4) Growth regulating substance
(a) Chitin synthesis inhibitor: Chlorfluazuron, diflubenzuron, flucycloxuron, flufenoxuron, hexaflumuron, lufenuron, novaluron, teflubenzuron, triflumuron, bistrifluron, noviflumuron, buprofezin, hexythiazox, etoxazole, clofentezine, fluazuron, and penfluoron;
(b) Ecdysone antagonist: Halofenozide, methoxyfenozide, tebufenozide, chromafenozide, and azadirachtin;
(c) Juvenile hormone analogue: Pyriproxyfen, methoprene, diofenolan, epofenonane, hydroplane, kinoprene, and triprene;
(d) Lipid biosynthesis inhibitor: Spirodiclofen, spiromesifen, spirotetramat, and flonicamid;

(5) Nicotine receptor agonist/antagonistic compound: Acetamiprid, clothianidin, dinotefuran, imidacloprid, nitenpyram, thiacloprid, thiamethoxam, nithiazine, nicotine, bensultap, cartap, and flupyradifurone;

(6) GABA antagonistic compound:
(a) Acetoprole, ethiprole, fipronil, vaniliprole, pyrafluprole, and pyriprole;
(b) Organochlorine base: Camphechlor, chlordane, endosulfan, HCH, γ-HCH, heptachlor, and methoxychlor.

(7) Macrocyclic lactone insecticide: Abamectin, emamectin benzoate, milbemectin, lepimectin, spinosad, ivermectin, selamectin, doramectin, eprinomectin, and moxidectin;

(8) METI I compound: Fenazaquin, pyridaben, tebufenpyrad, tolfenpyrad, flufenerim, hydramethylnon, fenpyroximate, pyrimidifen, and dicofol;

(9) METI II and III compounds: Acequinocyl, fluacrypyrim, and rotenone;

(10) Uncoupling agent compound: Chlorfenapyr, binapacryl, dinobuton, dinocap, and DNOC;

(11) Oxidative phosphorylation inhibitor compound: Cyhexatin, diafenthiuron, fenbutatin-oxide, propargite, and azocyclotin;

(12) Ecdysis disturbance compound: Cyromazine;

(13) Mixed function oxidase inhibitor compound: Piperonyl butoxide;

(14) Sodium channel blocker compound: Indoxacarb and metaflumizone;

(15) Microbial pesticide: A BT agent, an insect pathogenic viral agent, an insect pathogenic filamentous fungus agent, a nematode pathogenic filamentous fungus agent, *bacillus* species, *beauveria bassiana, metarhizium anisopliae, paecilomyces* species, *thuringiensin*, and *verticillium* species;

(16) Latrophilin receptor agonist: Depsipeptide, cyclic depsipeptide, 24-membered cyclic depsipeptide, and emodepside;

(17) Octopamine agonist: Amitraz;

(18) Ryanodine derivative agonist: Flubendiamide, chlorantraniliprole, and cyantraniliprole;

(19) Inhibitor of magnesium stimulative ATPase: Thiocyclam, thiosultap, and nereistoxin;

(20) Feeding inhibitor: Pymetrozine;

(21) Mite growth inhibitor: Clofentezine and etoxazole;

(22) Others: Benclothiaz, bifenazate, pyridalyl, sulfur, cyenopyrafen, cyflumetofen, amidoflumet, tetradifon, chlordimeform, 1,3-dichloropropene, DCIP, phenisobromolate, benzomate, metaldehyde, spinetoram, pyrifluquinazon, benzoxymate, bromopropylate, chinomethionate, chlorobenzilate, chloropicrin, clothiazoben, dicyclanil, fenoxacrim, fentrifanil, flubenzimine, flufenzine, gossyplure, japonilure, metoxadiazone, petroleum, potassium oleate, sulfluramid, tetrasul, and triarathene;

(23) Anthelmintic:
(a) Benzimidazole base: Fenbendazole, albendazole, triclabendazole, and oxibendazole;
(b) Salicylanilide base: Closantel and oxyclozanide;
(c) Substituted phenol base: Nitoroxinil;
(d) Pyrimidine base: Pyrantel;
(e) Imidazothiazole base: Levamisole;
(f) tetrahydropyrimidine: Praziquantel;
(g) Other anthelmintics: Cyclodiene, ryania, clorsulon, and metronidazole;

Plant Growth Regulator:
Abscisic acid, indolebutyric acid, uniconazole, ethylchlozate, ethephon, cloxyfonac, chlormequat, chlorella extract, calcium peroxide, cyanamide, dichlorprop, gibberellin, daminozide, decyl alcohol, trinexapac ethyl, mepiquat chloride, paclobutrazol, paraffin wax, piperonyl butoxide, pyraflufen ethyl, flurprimidol, prohydrojasmon, a prohexadione calcium salt, benzylaminopurine, pendimethalin, forchlorfenuron, maleic hydrazide potassium, 1-naphthyl acetamide, 4-CPA, MCPB, choline, oxyquinoline sulfate, ethychlozate, butralin, 1-methylcyclopropene, and aviglycine hydrochloride;

EXAMPLES

Next, although the present invention will be described in further detail by showing the following examples, the present invention is not limited to the following examples.

Example 1

0.40 g (1.25 mmol) of the compound represented by the formula (I) was put into a 30 mL flask, then, 10 mL of pyridine was added thereto at room temperature, and 0.15 g (1.88 mmol) of acetyl chloride was further added thereto. The mixture was heated at 60° C. to 70° C. in a nitrogen atmosphere, and stirred for 8 hours. After cooling the reaction mixture down to room temperature, the reaction mixture was poured into a mixed solution of 150 mL of ethyl acetate and 100 mL of water, then, the organic layer thereof was recovered, and the aqueous layer was extracted with 100 mL of ethyl acetate. The collected organic layer was washed with 50 mL of brine, and dried over magnesium sulfate. The resultant product was filtered and concentrated, and the obtained residue was washed with an acetone solution and filtered, whereby 0.31 g (yield of 71%) of a compound (compound No. 109) represented by the formula (II) was obtained as a colorless solid.

[Chem. 10]

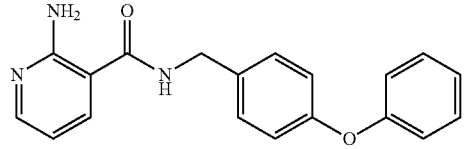

(I)

[Chem. 11]

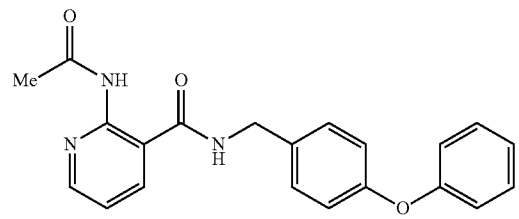

(II)

The pyridine compound obtained in the above-described Example and pyridine compounds synthesized in the same manner as in the above-described Example are shown in Table 1.

In Table 1, $R^1$, $R^2$, $R^3$, $R^4$, R, E, and $[A]_n$ represent those in the formula (1-A). In Table 1, Ph represents a phenyl group, Py represents a pyridyl group, Me represents a methyl group, and Et represents an ethyl group.

[Chem. 12]

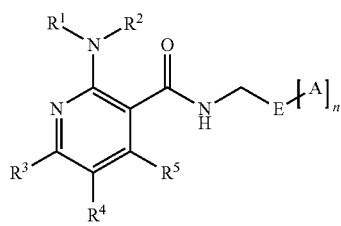

(1-A)

TABLE 1

| Compound number | $R^1$ | $R^2$ | $R^3$ | $R^4$ | $R^5$ | E | $[A]_n$ |
|---|---|---|---|---|---|---|---|
| 1 | CHO | H | H | H | H | Ph | — |
| 2 | CHO | H | H | H | H | Ph | 2-F |
| 3 | CHO | H | H | H | H | Ph | 3-F |
| 4 | CHO | H | H | H | H | Ph | 4-E |
| 5 | CHO | H | H | H | H | Ph | 2-Cl |
| 6 | CHO | H | H | H | H | Ph | 3-Cl |
| 7 | CHO | H | H | H | H | Ph | 4-Cl |
| 8 | CHO | H | H | H | H | Ph | 2-CN |
| 9 | CHO | H | H | H | H | Ph | 3-CN |
| 10 | CHO | H | H | H | H | Ph | 4-CN |
| 11 | CHO | H | H | H | H | Ph | 2-Me |
| 12 | CHO | H | H | H | H | Ph | 3-Me |
| 13 | CHO | H | H | H | H | Ph | 4-Me |
| 14 | CHO | H | H | H | H | Ph | 2-OMe |
| 15 | CHO | H | H | H | H | Ph | 3-OMe |
| 16 | CHO | H | H | H | H | Ph | 4-OMe |
| 17 | CHO | H | H | H | H | Ph | 2-Ph |
| 18 | CHO | H | H | H | H | Ph | 3-Ph |
| 19 | CHO | H | H | H | H | Ph | 4-Ph |
| 20 | CHO | H | H | H | H | Ph | 2-OPh |
| 21 | CHO | H | H | H | H | Ph | 3-OPh |
| 22 | CHO | H | H | H | H | Ph | 4-OPh |
| 23 | CHO | H | H | H | H | Ph | 3-O-2-Py |
| 24 | CHO | H | H | H | H | Ph | 3-O-3-Py |
| 25 | CHO | H | H | H | H | Ph | 3-O-4-Py |
| 26 | CHO | H | H | H | H | Ph | 4-O-2-Py |
| 27 | CHO | H | H | H | H | Ph | 4-O-3-Py |
| 28 | CHO | H | H | H | H | Ph | 4-O-4-Py |
| 29 | CHO | H | H | H | H | Ph | 3-CH$_3$O—Ph |
| 30 | CHO | H | H | H | H | Ph | 4-CH$_3$O—Ph |
| 31 | CHO | H | Me | H | H | Ph | — |
| 32 | CHO | H | Me | H | H | Ph | 3-F |
| 33 | CHO | H | Me | H | H | Ph | 4-F |
| 34 | CHO | H | Me | H | H | Ph | 2-Me |
| 35 | CHO | H | Me | H | H | Ph | 3-Me |
| 36 | CHO | H | Me | H | H | Ph | 4-Me |
| 37 | CHO | H | Me | H | H | Ph | 2-OMe |
| 38 | CHO | H | Me | H | H | Ph | 3-OMe |
| 39 | CHO | H | Me | H | H | Ph | 4-OMe |
| 40 | CHO | H | Me | H | H | Ph | 4-Ph |
| 41 | CHO | H | Me | H | H | Ph | 4-OPh |
| 42 | CHO | H | Me | Me | H | Ph | 4-OPh |
| 43 | CHO | H | Me | H | Me | Ph | 4-OPh |
| 44 | CHO | H | Cl | H | H | Ph | 4-OPh |
| 45 | CHO | H | F | H | H | Ph | 4-OPh |
| 46 | CHO | H | Cl | H | Me | Ph | 4-OPh |

TABLE 1-continued

| Compound number | R¹ | R² | R³ | R⁴ | R⁵ | E | [A]ₙ |
|---|---|---|---|---|---|---|---|
| 47 | CHO | H | H | Cl | H | Ph | 4-OPh |
| 48 | CHO | H | H | H | F | Ph | 4-OPh |
| 49 | CHO | H | Me | Cl | H | Ph | 4-OPh |
| 50 | CHO | H | Et | H | H | Ph | — |
| 51 | CHO | H | Et | H | H | Ph | 4-F |
| 52 | CHO | H | Et | H | H | Ph | 4-Ph |
| 53 | CHO | H | Et | H | H | Ph | 4-OPh |
| 54 | CHO | H | OMe | H | H | Ph | — |
| 55 | CHO | H | OMe | H | H | Ph | 4-F |
| 56 | CHO | H | OMe | H | H | Ph | 4-Ph |
| 57 | CHO | H | OMe | H | H | Ph | 4-OPh |
| 58 | CHO | H | H | H | H | Ph | 4-CH₃O-2-Py |
| 59 | CHO | H | H | H | H | Ph | 4-CH₃O-2-(6-F—Py) |
| 60 | CHO | H | H | H | H | 2-Py | 3-OPh |
| 61 | CHO | H | H | H | H | 2-Py | 4-OPh |
| 62 | CHO | H | H | H | H | 2-Py | 5-OPh |
| 63 | CHO | H | H | H | H | 2-Py | 6-OPh |
| 64 | CHO | H | H | H | H | 3-Py | 2-OPh |
| 65 | CHO | H | H | H | H | 3-Py | 4-OPh |
| 66 | CHO | H | H | H | H | 3-Py | 5-OPh |
| 67 | CHO | H | H | H | H | 3-Py | 6-OPh |
| 68 | CHO | H | H | H | H | 4-Py | 2-OPh |
| 69 | CHO | H | H | H | H | 4-Py | 3-OPh |
| 70 | CHO | H | H | H | H | 2-furyl | 3-OPh |
| 71 | CHO | H | H | H | H | 2-furyl | 4-OPh |
| 72 | CHO | H | H | H | H | 2-furyl | 5-OPh |
| 73 | CHO | H | H | H | H | 3-furyl | 2-OPh |
| 74 | CHO | H | H | H | H | 3-furyl | 4-OPh |
| 75 | CHO | H | H | H | H | 3-furyl | 5-OPh |
| 76 | CHO | H | H | H | H | 1-pyrrolyl | 2-OPh |
| 77 | CHO | H | H | H | H | 1-pyrrolyl | 3-OPh |
| 78 | CHO | H | H | H | H | 2-pyrrolyl | 1-OPh |
| 79 | CHO | H | H | H | H | 2-pyrrolyl | 3-OPh |
| 80 | CHO | H | H | H | H | 2-pyrrolyl | 4-OPh |
| 81 | CHO | H | H | H | H | 2-pyrrolyl | 5-OPh |
| 82 | CHO | H | H | H | H | 3-pyrrolyl | 1-OPh |
| 83 | CHO | H | H | H | H | 3-pyrrplyl | 2-OPh |
| 84 | CHO | H | H | H | H | 5-tetrazolyl | 1-OPh |
| 85 | CHO | H | H | H | H | 1-tetrazolyl | 5-OPh |
| 86 | CHO | H | H | H | H | 2-thiazolyl | 4-OPh |
| 87 | CHO | H | H | H | H | 2-thiazolyl | 5-OPh |
| 88 | CHO | H | H | H | H | 4-thiazolyl | 2-OPh |
| 89 | CHO | H | H | H | H | 4-thiazolyl | 5-OPh |
| 90 | CHO | H | H | H | H | 5-thiazolyl | 2-OPh |
| 91 | CHO | H | H | H | H | 5-thiazolyl | 4-OPh |
| 92 | CHO | H | H | H | H | 1-pyrazolyl | 3-OPh |
| 93 | CHO | H | H | H | H | 1-pyrazolyl | 4-OPh |
| 94 | CHO | H | H | H | H | 1-pyrazolyl | 5-OPh |
| 95 | CHO | H | H | H | H | 3-pyrazolyl | 1-OPh |
| 96 | CHO | H | H | H | H | 3-pyrazolyl | 4-OPh |
| 97 | CHO | H | H | H | H | 3-pyrazolyl | 5-OPh |
| 98 | CHO | H | H | H | H | 4-pyrazolyl | 1-OPh |
| 99 | CHO | H | H | H | H | 4-pyrazolyl | 3-OPh |
| 100 | CHO | H | H | H | H | 4-pyrazolyl | 5-OPh |
| 101 | CHO | H | H | H | H | 5-pyrazolyl | 1-OPh |
| 102 | CHO | H | H | H | H | 5-pyrazolyl | 3-OPh |
| 103 | CHO | H | H | H | H | 5-pyrazolyl | 4-OPh |
| 104 | CHO | Me | H | H | H | Ph | 4-OPh |
| 105 | CHO | Me | Me | H | H | Ph | 4-OPh |
| 106 | CHO | Me | H | Me | H | Ph | 4-OPh |
| 107 | CHO | Me | Cl | H | H | Ph | 4-OPh |
| 108 | CHO | Me | F | H | H | Ph | 4-OPh |
| 109 | CHO | Me | H | Cl | H | Ph | 4-OPh |
| 110 | CHO | Me | H | F | H | Ph | 4-OPh |
| 111 | CHO | Me | H | H | H | Ph | — |
| 112 | CHO | Me | H | H | H | Ph | 4-F |
| 113 | CHO | Me | H | H | H | Ph | 2-Me |
| 114 | CHO | Me | H | H | H | Ph | 3-Me |
| 115 | CHO | Me | H | H | H | Ph | 4-Me |
| 116 | CHO | Me | H | H | H | Ph | 2-OMe |
| 117 | CHO | Me | H | H | H | Ph | 3-OMe |
| 118 | CHO | Me | H | H | H | Ph | 4-OMe |
| 119 | CHO | Me | H | H | H | Ph | 4-OPh |
| 120 | CHO | Me | Me | H | H | Ph | — |
| 121 | CHO | Me | Me | H | H | Ph | 4-OPh |
| 122 | COMe | H | H | H | H | Ph | — |
| 123 | COMe | H | H | H | H | Ph | 4-F |

TABLE 1-continued

| Compound number | R¹ | R² | R³ | R⁴ | R⁵ | E | [A]ₙ |
|---|---|---|---|---|---|---|---|
| 124 | COMe | H | H | H | H | Ph | 4-Cl |
| 125 | COMe | H | H | H | H | Ph | 4-CN |
| 126 | COMe | H | H | H | H | Ph | 4-Ph |
| 127 | COMe | H | H | H | H | Ph | 4-OPh |
| 128 | COMe | H | H | H | H | Ph | 4-CH₃O—Ph |
| 129 | COMe | H | H | H | H | Ph | 4-CH₃O-2-Py |
| 130 | COMe | H | H | H | H | Ph | 4-CH₃O-2-(6-F—Py) |
| 131 | COMe | H | Me | H | H | Ph | — |
| 132 | COMe | H | Me | H | H | Ph | 4-F |
| 133 | COMe | H | Me | H | H | Ph | 4-CN |
| 134 | COMe | H | Me | H | H | Ph | 3-Me |
| 135 | COMe | H | Me | H | H | Ph | 4-Me |
| 136 | COMe | H | Me | H | H | Ph | 2-OMe |
| 137 | COMe | H | Me | H | H | Ph | 3-OMe |
| 138 | COMe | H | Me | H | H | Ph | 4-OMe |
| 139 | COMe | H | Me | H | H | Ph | 4-OPh |
| 140 | COMe | H | Et | H | H | Ph | 4-OPh |
| 141 | COMe | Me | H | H | H | Ph | 4-OPh |
| 142 | COMe | Me | Me | H | H | Ph | 4-OPh |
| 143 | COMe | Me | Et | H | H | Ph | 4-OPh |
| 144 | COMe | H | H | H | H | 2-Py | 5-OPh |
| 145 | COEt | H | H | H | H | Ph | — |
| 146 | COEt | H | H | H | H | Ph | 4-F |
| 147 | COEt | H | H | H | H | Ph | 4-Me |
| 148 | COEt | H | H | H | H | Ph | 2-OMe |
| 149 | COEt | H | H | H | H | Ph | 3-OMe |
| 150 | COEt | H | H | H | H | Ph | 4-OMe |
| 151 | COEt | H | H | H | H | Ph | 4-OPh |
| 152 | COEt | H | H | H | H | Ph | 5-OPh |
| 153 | COEt | H | Me | H | H | Ph | 4-OPh |
| 154 | COEt | H | Et | H | H | Ph | 4-OPh |
| 155 | COEt | Me | H | H | H | 2-Py | 5-OPh |
| 156 | COCF₃ | H | H | H | H | Ph | 4-CN |
| 157 | COCF₃ | H | H | H | H | Ph | 4-OPh |
| 158 | COCF₃ | H | Me | H | H | Ph | 4-OPh |
| 159 | COCF₃ | Me | H | H | H | Ph | 4-OPh |
| 160 | COCF₃ | Me | F | H | H | Ph | 4-OPh |
| 161 | COCF₃ | Me | Me | H | H | Ph | — |
| 162 | COCF₃ | Me | Me | H | H | Ph | 4-F |
| 163 | COCF₃ | Me | Me | H | H | Ph | 4-CN |
| 164 | COCF₃ | Me | Me | H | H | Ph | 4-Me |
| 165 | COCF₃ | Me | Me | H | H | Ph | 2-OMe |
| 166 | COCF₃ | Me | Me | H | H | Ph | 3-OMe |
| 167 | COCF₃ | Me | Me | H | H | Ph | 4-OMe |
| 168 | COCF₃ | Me | Me | H | H | Ph | 4-OPh |
| 169 | COCF₃ | Me | Me | H | H | Ph | 4-CH₃O—Ph |
| 170 | COCF₃ | Me | Me | H | H | Ph | 4-CH₃O-2-(6-F—Py) |
| 171 | COPh | H | H | H | H | Ph | 4-CN |
| 172 | COPh | H | H | H | H | Ph | 4-F |
| 173 | COPh | H | H | H | H | Ph | 4-Me |
| 174 | COPh | H | H | H | H | Ph | 2-OMe |
| 175 | COPh | H | H | H | H | Ph | 3-OMe |
| 176 | COPh | H | H | H | H | Ph | 4-OMe |
| 177 | COPh | H | H | H | H | Ph | 4-OPh |
| 178 | COPh | H | H | H | H | Ph | 4-CH₃O—Ph |
| 179 | COPh | H | H | H | H | Ph | 4-CH₃O-2-(6-F—Py) |
| 180 | COPh | Me | H | H | H | Ph | 4-CN |
| 181 | COPh | Me | H | H | H | Ph | 4-Me |
| 182 | COPh | Me | H | H | H | Ph | 2-OMe |
| 183 | COPh | Me | H | H | H | Ph | 3-OMe |
| 184 | COPh | Me | H | H | H | Ph | 4-OMe |
| 185 | COPh | Me | H | H | H | Ph | 4-OPh |
| 186 | COPh | Me | H | H | H | Ph | 4-CH₃O—Ph |
| 187 | COPh | Me | H | H | H | Ph | 4-CH₃O-2-(6-F—Py) |
| 188 | CO-2-Py | H | H | H | H | Ph | 4-OPh |
| 189 | CO-2-Py | Me | H | H | H | Ph | 4-OPh |
| 190 | CO-2-Py | H | Me | H | H | Ph | 4-OPh |
| 191 | CO-2-tetrahydrofuranyl | H | H | H | H | Ph | 4-Cl |
| 192 | CO-2-tetrahydrofuranyl | H | H | H | H | Ph | 4-F |
| 193 | CO-2-tetrahydrofuranyl | H | H | H | H | Ph | 4-Me |
| 194 | CO-2-tetrahydrofuranyl | H | H | H | H | Ph | 4-OMe |
| 195 | CO-2-tetrahydrofuranyl | H | H | H | H | Ph | 4-OPh |
| 196 | CO-2-tetrahydrofuranyl | Me | H | H | H | Ph | 4-OPh |
| 197 | CO-2-tetrahydrofuranyl | H | Me | H | H | Ph | 4-OPh |
| 198 | CO-2-thienyl | H | H | H | H | Ph | 4-Cl |
| 199 | CO-2-thienyl | H | H | H | H | Ph | 4-F |
| 200 | CO-2-thienyl | H | H | H | H | Ph | 4-CN |

TABLE 1-continued

| Compound number | R¹ | R² | R³ | R⁴ | R⁵ | E | [A]ₙ |
|---|---|---|---|---|---|---|---|
| 201 | CO-2-thienyl | H | H | H | H | Ph | 4-Me |
| 202 | CO-2-thienyl | H | H | H | H | Ph | 2-OMe |
| 203 | CO-2-thienyl | H | H | H | H | Ph | 3-OMe |
| 204 | CO-2-thienyl | H | H | H | H | Ph | 4-OMe |
| 205 | CO-2-thienyl | H | H | H | H | Ph | 4-OPh |
| 206 | CO-2-thienyl | Me | H | H | H | Ph | 4-Cl |
| 207 | CO-2-thienyl | Me | H | H | H | Ph | 4-CN |
| 208 | CO-2-thienyl | Me | H | H | H | Ph | 4-Me |
| 209 | CO-2-thienyl | Me | H | H | H | Ph | 2-OMe |
| 210 | CO-2-thienyl | Me | H | H | H | Ph | 3-OMe |
| 211 | CO-2-thienyl | Me | H | H | H | Ph | 4-OMe |
| 212 | CO-2-thienyl | Me | H | H | H | Ph | 4-OPh |
| 213 | CO-2-thienyl | H | Me | H | H | Ph | 4-Cl |
| 214 | CO-2-thienyl | H | Me | H | H | Ph | 4-F |
| 215 | CO-2-thienyl | H | Me | H | H | Ph | 4-CN |
| 216 | CO-2-thienyl | H | Me | H | H | Ph | 4-Me |
| 217 | CO-2-thienyl | H | Me | H | H | Ph | 4-OMe |
| 218 | CO-2-thienyl | H | Me | H | H | Ph | 4-OPh |
| 219 | CO-cyclopentyl | H | H | H | H | Ph | 4-Cl |
| 220 | CO-cyclopentyl | H | H | H | H | Ph | 4-F |
| 221 | CO-cyclopentyl | H | H | H | H | Ph | 4-CN |
| 222 | CO-cyclopentyl | H | H | H | H | Ph | 4-Me |
| 223 | CO-cyclopentyl | H | H | H | H | Ph | 2-OMe |
| 224 | CO-cyclopentyl | H | H | H | H | Ph | 3-OMe |
| 225 | CO-cyclopentyl | H | H | H | H | Ph | 4-OMe |
| 226 | CO-cyclopentyl | H | H | H | H | Ph | 4-OPh |
| 227 | CO-cyclopentyl | Me | H | H | H | Ph | 4-OPh |
| 228 | CO-cyclopentyl | H | Me | H | H | Ph | 4-OPh |
| 229 | COCH₂Ph | H | H | H | H | Ph | 4-Cl |
| 230 | COCH₂Ph | H | H | H | H | Ph | 4-F |
| 231 | COCH₂Ph | H | H | H | H | Ph | 4-CN |
| 232 | COCH₂Ph | H | H | H | H | Ph | 4-Me |
| 233 | COCH₂Ph | H | H | H | H | Ph | 2-OMe |
| 234 | COCH₂Ph | H | H | H | H | Ph | 3-OMe |
| 235 | COCH₂Ph | H | H | H | H | Ph | 4-OMe |
| 236 | COCH₂Ph | H | H | H | H | Ph | 4-OPh |
| 237 | COCH₂Ph | Me | H | H | H | Ph | 4-OPh |
| 238 | COCH₂Ph | H | Me | H | H | Ph | 4-OPh |
| 239 | COCH₂Cl | H | H | H | H | Ph | 4-Cl |
| 240 | COCH₂Cl | H | H | H | H | Ph | 4-Fl |
| 241 | COCH₂Cl | H | H | H | H | Ph | 4-CN |
| 242 | COCH₂Cl | H | H | H | H | Ph | 4-Me |
| 243 | COCH₂Cl | H | H | H | H | Ph | 4-OMe |
| 244 | COCH₂Cl | H | H | H | H | Ph | 4-OPh |
| 245 | COCH₂Cl | Me | H | H | H | Ph | 4-OPh |
| 246 | COCH₂Cl | H | H | H | H | Ph | 4-CH₃O—Ph |
| 247 | COCH₂Cl | Me | H | H | H | Ph | 4-CH₃O—Ph |
| 248 | COCH₂OMe | H | H | H | H | Ph | 4-Cl |
| 249 | COCH₂OMe | H | H | H | H | Ph | 4-F |
| 250 | COCH₂OMe | H | H | H | H | Ph | 4-CN |
| 251 | COCH₂OMe | H | H | H | H | Ph | 4-Me |
| 252 | COCH₂OMe | H | H | H | H | Ph | 4-OMe |
| 253 | COCH₂OMe | H | H | H | H | Ph | 4-Ph |
| 254 | COCH₂OMe | Me | H | H | H | Ph | 4-Ph |
| 255 | COCH₂OMe | H | Me | H | H | Ph | 4-Ph |
| 256 | COCH₂OMe | H | H | H | H | Ph | 4-OPh |
| 257 | COCH₂OMe | Me | H | H | H | Ph | 4-OPh |
| 258 | COCH₂OMe | H | Me | H | H | Ph | 4-OPh |
| 259 | COCH₂OMe | H | H | H | H | Ph | 4-CH₃O—Ph |
| 260 | COCH₂OMe | Me | H | H | H | Ph | 4-CH₃O—Ph |
| 261 | COCH₂OMe | H | H | H | H | Ph | 2-OMe |
| 262 | COCH₂OMe | H | H | H | H | Ph | 3-OMe |
| 263 | COCH₂OMe | H | H | H | H | Ph | 4-OMe |
| 264 | COCH₂OPh | H | H | H | H | Ph | 4-Cl |
| 265 | COCH₂OPh | H | H | H | H | Ph | 4-F |
| 266 | COCH₂OPh | H | H | H | H | Ph | 4-Me |
| 267 | COCH₂OPh | H | H | H | H | Ph | 2-OMe |
| 268 | COCH₂OPh | H | H | H | H | Ph | 3-OMe |
| 269 | COCH₂OPh | H | H | H | H | Ph | 4-OMe |
| 270 | COCH₂OPh | H | H | H | H | Ph | 4-OPh |
| 271 | COOMe | H | H | H | H | Ph | 4-Ph |
| 272 | COOMe | H | Me | H | H | Ph | 4-Ph |
| 273 | COOMe | H | H | H | H | Ph | 4-OPh |
| 274 | COOMe | Me | H | H | H | Ph | 4-OPh |
| 275 | COOMe | H | OMe | H | H | Ph | 4-OPh |
| 276 | (CO)O$^t$Bu | H | H | H | H | Ph | 4-Ph |
| 277 | (CO)O$^t$Bu | H | Me | H | H | Ph | 4-Ph |

TABLE 1-continued

| Compound number | $R^1$ | $R^2$ | $R^3$ | $R^4$ | $R^5$ | E | $[A]_n$ |
|---|---|---|---|---|---|---|---|
| 278 | (CO)O$^t$Bu | H | H | H | H | Ph | 4-OPh |
| 279 | (CO)O$^t$Bu | Me | H | H | H | Ph | 4-OPh |
| 280 | (CO)O$^t$Bu | H | Me | H | H | Ph | 4-OPh |
| 281 | SO$_2$Me | H | H | H | H | Ph | 4-OPh |
| 282 | SO$_2$N(Me)$_2$ | H | H | H | H | Ph | 4-Ph |
| 283 | SO$_2$N(Me)$_2$ | H | Me | H | H | Ph | 4-Ph |
| 284 | SO$_2$N(Me)$_2$ | H | H | H | H | Ph | 4-OPh |
| 285 | SO$_2$N(Me)$_2$ | Me | H | H | H | Ph | 4-OPh |
| 286 | SO$_2$N(Me)$_2$ | H | Me | H | H | Ph | 4-OPh |
| 287 | SO$_2$N(Me)$_2$ | H | OMe | H | H | Ph | 4-OPh |

Melting points and refractive indexes of some of the compounds shown in Table 1 were measured. In addition, $^1$H-NMR measurement was performed on amorphous compounds (shown as Amorphous in Table 2). Physical properties of these are shown in the following Table 2.

TABLE 2

| Compound number | Melting Point (° C.) | Refractive index (nD) | $^1$H-NMR(CDCl$_3$)δ |
|---|---|---|---|
| 22 | 80-82 | | |
| 41 | 164-165 | | |
| 127 | 182-184 | | |
| 130 | 130-132 | | |
| 139 | 135-136 | | |
| 157 | 163-165 | | |
| 158 | 82-85 | 1.5717 (20.6° C.) | |
| 177 | 156-158 | | |
| 188 | 172-174 | | |
| 195 | 174-175 | | |
| 205 | 167-169 | | |
| 226 | 155-157 | | |
| 236 | 170-172 | | |
| 256 | 153-155 | | |
| 258 | 159-160 | | |
| 261 | Amorphous | | 3.50 (s, 3H), 3.87 (s, 3H), 4.04 (s, 2H), 4.60 (d, 2H), 6.7-7.3 (m, 6H), 7.77 (d, 1H), 8.54 (m, 1H), 11.42 (bs, 1H) |
| 262 | Amorphous | | 3.52 (s, 3H), 3.79 (s, 3H), 4.05 (s, 2H), 4.58 (d, 2H), 6.58 (bs, 1H), 6.8-7.1 (m, 4H), 7.25 (m, 1H), 7.83 (d, 1H), 8.53 (m, 1H), 11.26 (bs, 1H) |
| 263 | 119-122 | | |
| 270 | 146-148 | | |
| 273 | 134-137 | | |

(Formulation)

Next, although some of formulation examples of the agricultural fungicide according to the present invention will be shown, additives and additive proportions are not limited to these formulation examples and can be extensively changed. In addition, the "parts" in the formulation examples indicates "parts by mass".

Formulation Example 1

Wettable Powder

| | |
|---|---|
| Compound of the present invention | 40 parts |
| Clay | 48 parts |
| Dioctyl sodium sulfosuccinate | 4 parts |
| Sodium lignin sulfonate | 8 parts |

The above materials were uniformly mixed and finely pulverized, whereby a wettable powder having 40% of an active ingredient was obtained.

Formulation Example 2

Emulsifiable Concentrate

The above materials were mixed and dissolved, whereby an emulsifiable concentrate having 10% of an active ingredient was obtained.

| | |
|---|---|
| Compound of the present invention | 10 parts |
| Solvesso 200 | 53 parts |
| Cyclohexanone | 26 parts |
| Calcium dodecyl benzene sulfonate | 1 part |
| Polyoxyethylene alkylallyl ether | 10 parts |

Formulation Example 3

Dustable Powder

| Compound of the present invention | 10 parts |
|---|---|
| Clay | 90 parts |

The above materials were uniformly mixed and finely pulverized, whereby a dustable powder having 10% of an active ingredient was obtained.

Formulation Example 4

Granule

| Compound of the present invention | 5 parts |
|---|---|
| Clay | 73 parts |
| Bentonite | 20 parts |
| Dioctyl sodium sulfosuccinate | 1 part |
| Potassium phosphate | 1 part |

The above materials were fully pulverized and mixed, then, water was added thereto, and the mixture was fully kneaded and subjected to granulation and drying, whereby granules having 5% of an active ingredient were obtained.

Formulation Example 5

Suspension Concentrate

| Compound of the present invention | 10 parts |
|---|---|
| Polyoxyethylene alkylallyl ether | 4 parts |
| Sodium polycarboxylate | 2 parts |
| Glycerin | 10 parts |
| Xanthan gum | 0.2 parts |
| Water | 73.8 parts |

The above materials were mixed, and the mixture was wet-pulverized until the particle size became equal to or less than 3 microns, whereby a suspension concentrate having 10% of an active ingredient was obtained.

Formulation Example 6

Water Dispersible Granule

| Compound of the present invention | 40 parts |
|---|---|
| Clay | 36 parts |
| Potassium chloride | 10 parts |
| Sodium alkylbenzene sulfonate | 1 part |
| Sodium lignin sulfonate | 8 parts |
| Formaldehyde condensate of sodium alkylbenzene sulfonate | 5 parts |

The above materials were uniformly mixed and finely pulverized, then, an suitable amount of water was added thereto, and the mixture was kneaded, whereby a clay-like material was obtained. The clay-like material was granulated, whereby a water dispersible granule having 40% of an active ingredient was obtained.

(Biological Analysis 1) Cucumber Gray Mold Disease Control Test

An emulsion of the compound of the present invention was sprayed to a cucumber seedling (variety "Sagamihanjiro", cotyledon stage) grown in unglazed pot at a concentration of 500 ppm of an active ingredient, and natural drying was performed at room temperature. Thereafter, a conidia suspension of cucumber gray mold fungi (*Botrytis cinerea*) was inoculated by dropping, followed by maintaining at 20° C. for 4 days in a dark room with high humidity. The lesion appearance state on a leaf was compared to untreated one and investigated, and controlling effect was checked.

The cucumber gray mold disease control test was performed on the compounds of compound numbers 22, 127, 130, 139, 157, 158, 195, 256, 258, 270, and 273. As a result, all the compounds exhibited equal to or greater than 75% of a control value.

INDUSTRIAL APPLICABILITY

A pyridine compound or salts thereof of the present invention are useful novel compounds as an active ingredient of an agricultural fungicide. In addition, the agricultural fungicide of the present invention has a definitive and excellent control effects, does not cause phytotoxicity to plants, exhibits low toxicity to human bodies, animals, and fish, has little influence on the environment, and is a safe drug. Therefore, the present invention is highly useful.

The invention claimed is:
1. A pyridine compound represented by the formula (1) or a salt thereof

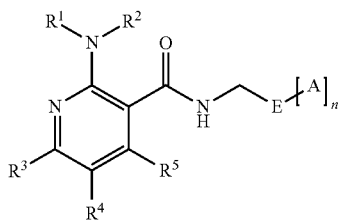

wherein
$R^1$ represents a formyl group, a C1-8 alkylcarbonyl group which is unsubstituted or has a substituent, a C3-8 cycloalkylcarbonyl group which is unsubstituted or has a substituent, a C6-10 arylcarbonyl group which is unsubstituted or has a substituent, a 5 to 10-membered heterocyclic carbonyl group which is unsubstituted or has a substituent, a C3-8 cycloalkyl C1-6 alkylcarbonyl group which is unsubstituted or has a substituent, a C6-10 aryl C1-6 alkylcarbonyl group which is unsubstituted or has a substituent, a 5 to 10-membered heterocyclic C1-6 alkylcarbonyl group which is unsubstituted or has a substituent, a C1-8 alkyloxycarbonyl group which is unsubstituted or has a substituent, a C3-8 cycloalkyloxycarbonyl group which is unsubstituted or has a substituent, a C6-10 aryloxycarbonyl group which is unsubstituted or has a substituent, a 5 to 10-membered heterocyclic oxycarbonyl group which is unsubstituted or has a substituent, a C1-8 alkylthiocarbonyl group which is unsubstituted or has a substituent, a di C1-8 alkylsulfamoyl group which is unsubstituted or has a substituent, a C1-8 alkylsulfonyl group which is unsubstituted or has a substituent, a C3-8 cycloalkylsulfonyl group which is unsubstituted or has a substituent, a C6-10 arylsulfonyl groups which is unsubstituted or has a substituent, or a 5 to 10-membered heterocyclic sulfonyl group which is unsubstituted or has a substituent, $R^2$ represents a hydrogen atom, a C1-8 alkyl group which is unsubstituted or has a substituent, or a C1-8 alkylcarbonyl group which is unsubstituted or has a substituent, Each of $R^3$, $R^4$, and $R^5$ independently represents a hydrogen atom, a C1-8 alkyl group which is unsubstituted or has a substituent, or a halogen atom, E represents a furyl group, a pyrrolyl group, a tetrazolyl group, a thiazolyl group, a pyrazolyl group, a phenyl group, or a pyridyl group, A represents a cyano group, a C1-8 alkyl group which is unsubstituted or has a substituent, a C1-8 alkoxy group which has a substituent, a C3-8 cycloalkyl group which is unsubstituted or has a substituent, a C3-8 cycloalkoxy group which is unsubstituted or has a substituent, a C6-10 aryl group which is unsubstituted or has a substituent, a C6-10 aryloxy group which is unsubstituted or has a substituent, a 5 to 10-membered heterocyclic group which is unsubstituted or has a substituent, or a 5 to 10 membered heterocyclyloxy group which is unsubstituted or has a substituent, n represents the number of A, and is any integer of 0 to 5, when n is equal to or greater than 2, A's may be the same as or different from each other.

2. The pyridine compound or a salt thereof according to claim 1, wherein in the formula (1), E is a phenyl group.

3. The pyridine compound or a salt thereof according to claim 1, wherein in the formula (1), A is any one of a cyano group, a C1-8 alkyl group which is unsubstituted or has a substituent, a C1-8 alkoxy group which has a substituent, a phenyl group which is unsubstituted or has a substituent, a phenoxy group which is unsubstituted or has a substituent, a 5 or 6-membered heteroaryl group which is unsubstituted or has a substituent, or a 5 or 6-membered heteroaryloxy group which is unsubstituted or has a substituent, and n is any integer of 1 to 5.

4. The pyridine compound or a salt thereof according to claim 1, wherein in the formula (1), $R^3$ is a hydrogen atom, or a C1-8 alkyl group which is unsubstituted or has a substituent.

5. An agricultural fungicide comprising:
at least one selected from the pyridine compound or a salt thereof according to claim 1 as an active ingredient.

* * * * *